United States Patent
White et al.

(10) Patent No.: US 11,335,441 B2
(45) Date of Patent: May 17, 2022

(54) HEALTH SAFETY SYSTEM, SERVICE, AND METHOD

(71) Applicant: TensorX, Inc., Nashville, TN (US)

(72) Inventors: N. Edward White, Austin, TX (US); G. Edward Powell, Nashville, TN (US); Van L. Marshall, Jackson, MI (US); Mark T. Lane, Franklin, TN (US); John M. Clerici, Vienna, VA (US)

(73) Assignee: TensorX, Inc., Nashville, TN (US)

( * ) Notice: Subject to any disclaimer, the term of this patent is extended or adjusted under 35 U.S.C. 154(b) by 0 days.

(21) Appl. No.: 17/341,599

(22) Filed: Jun. 8, 2021

(65) Prior Publication Data

US 2021/0391041 A1    Dec. 16, 2021

Related U.S. Application Data

(63) Continuation-in-part of application No. 17/176,088, filed on Feb. 15, 2021, which is a continuation of
(Continued)

(51) Int. Cl.
*G16H 10/40* (2018.01)
*G16H 10/60* (2018.01)
(Continued)

(52) U.S. Cl.
CPC ........... *G16H 10/40* (2018.01); *A61B 5/1171* (2016.02); *A61B 5/1172* (2013.01); *A61B 5/4842* (2013.01); *G06F 16/2365* (2019.01); *G07C 9/37* (2020.01); *G07C 9/38* (2020.01); *G16H 10/60* (2018.01); *G16H 50/20* (2018.01); *G16H 50/30* (2018.01); *G16H 50/50* (2018.01); *H04L 9/3268* (2013.01); *H04L 63/0428* (2013.01);
(Continued)

(58) Field of Classification Search
CPC ........ G16H 10/40; G16H 10/60; G16H 50/20; G16H 50/30; G06F 16/2365
See application file for complete search history.

(56) References Cited

U.S. PATENT DOCUMENTS

| | | | |
|---|---|---|---|
| 6,926,203 B1 * | 8/2005 | Sehr | G06Q 10/025 235/382 |
| 2015/0227945 A1 * | 8/2015 | Shea, III | G06Q 30/018 705/317 |
| 2020/0372743 A1 * | 11/2020 | Miller | G06K 9/00288 |

OTHER PUBLICATIONS

M. Eisenstadt, M. Ramachandran, N. Chowdhury, A. Third and J. Domingue, "COVID-19 Antibody Test/Vaccination Certification: There's an App for That," in IEEE Open Journal of Engineering in Medicine and Biology, vol. 1, pp. 148-155, Jun. 1, 2020, doi: 10.1109/OJEMB.2020.2999214. (Year: 2020).*
(Continued)

*Primary Examiner* — Evangeline Barr
(74) *Attorney, Agent, or Firm* — John K. Harrop

(57) ABSTRACT

A health safety method executed by a processor includes receiving, by the processor, from a medical facility, a certificate of vaccination for a particular disease for an individual, the vaccination conferring immunity to the individual for the disease; receiving by the processor an access request from a venue for the individual; and responding to the venue access request by providing a health safety certification including the certificate of vaccination for the individual and an effective date range of the certificate of vaccination.

30 Claims, 19 Drawing Sheets

Related U.S. Application Data application No. 16/900,803, filed on Jun. 12, 2020, now Pat. No. 10,923,216.

(60) Provisional application No. 63/040,871, filed on Jun. 18, 2020.

(51) Int. Cl.
| | |
|---|---|
| *G16H 50/20* | (2018.01) |
| *G06F 16/23* | (2019.01) |
| *G16H 50/50* | (2018.01) |
| *G07C 9/37* | (2020.01) |
| *G07C 9/38* | (2020.01) |
| *H04L 9/32* | (2006.01) |
| *A61B 5/1172* | (2016.01) |
| *A61B 5/1171* | (2016.01) |
| *A61B 5/00* | (2006.01) |
| *G16H 50/30* | (2018.01) |
| *H04L 29/06* | (2006.01) |
| *G16H 50/80* | (2018.01) |
| *G06Q 50/26* | (2012.01) |
| *G06V 20/40* | (2022.01) |

(52) U.S. Cl.
CPC ........... *G06Q 50/265* (2013.01); *G06V 20/40* (2022.01); *G16H 50/80* (2018.01); *H04L 2209/38* (2013.01)

(56) References Cited

OTHER PUBLICATIONS

Kumanan Wilson, Katherine M. Atkinson, and Cameron P. Bell, "Travel Vaccines Enter the Digital Age: Creating a Virtual Immunization Record", Am J. Trap Med. Hyg., 94(3), 2016, pp. 485-488, doi:10/4269/ajtmh.15-0510 (Year: 2016).*

* cited by examiner

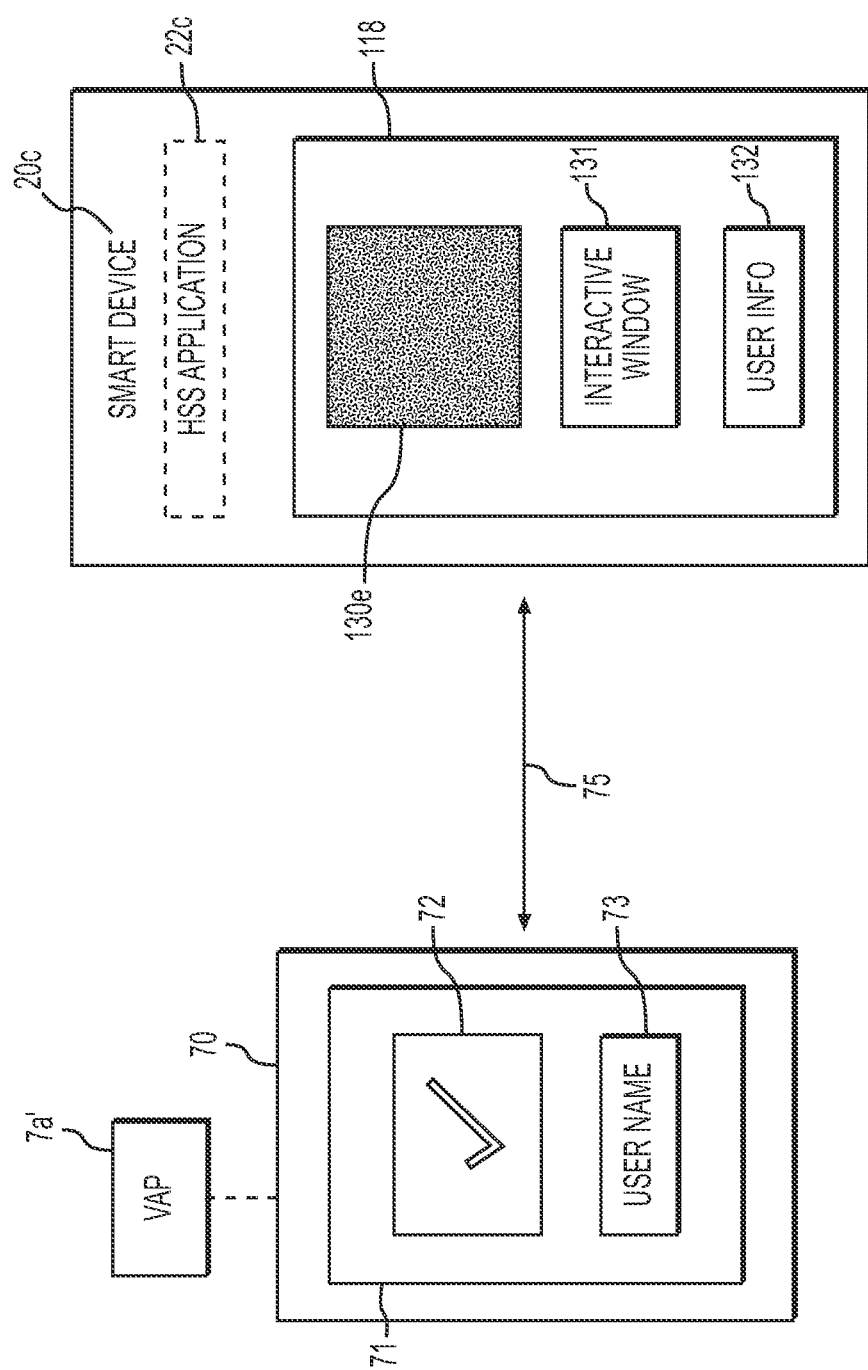

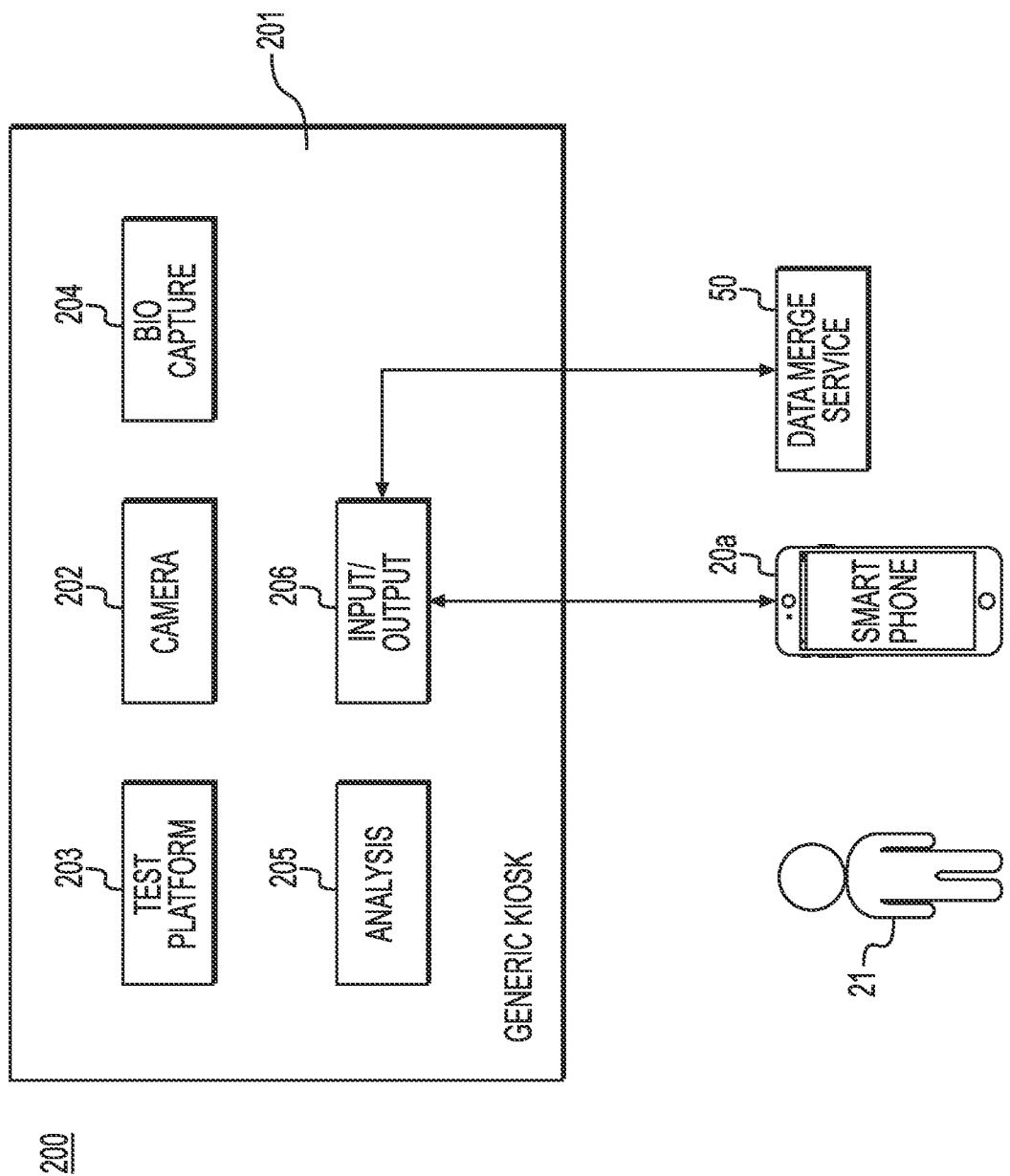

HEALTH SAFETY SYSTEM, SERVICE, AND METHOD

RELATED APPLICATIONS

This application is a continuation-in-part of U.S. patent application Ser. No. 17/176,088, filed Feb. 15, 2021, titled Health Status System, Platform, and Method, which is a continuation of U.S. patent application Ser. No. 16/900,803, filed Jun. 12, 2020, titled Health Status System, Platform, and Method, now U.S. Pat. No. 10,923,216, issued Feb. 16, 2021. This application also claims priority to U.S. Provisional Patent Application 63/040,871, filed Jun. 18, 2020, titled Health Status System, Platform, and Method. The disclosures of the above-identified applications are incorporated by reference.

BACKGROUND

Health safety threats, including infection resulting from an epidemic, pandemic, bio-terrorism or biological warfare are driving organization to consider restricting access to their venues, modes of transportation, and activities to individuals who have been tested and are, within the limits of the test: sensitivity, specificity, surety, etc. infection free and/or are immune to infection. One testing approach is to test at the point of entry by clinical personnel. For example, the White House recently announced that during the COVID-19 pandemic, visitors would be screened for the virus prior to being allowed to meet with the President. In this situation, tests are performed on site and the results reported directly to the visitor being tested. Each visitor's nose or throat is swabbed and the resulting sample is analyzed for indications of infection. In some tests, body fluids, blood or mucus may be sampled/tested, including, for example, to test for sexually-transmitted diseases and other diseases. These onsite tests may take 15 to 20 minutes from sample collection to result.

Other sites such as nursing homes, hospitals and meat processing facilities may regularly test employees before allowing them access to the premises. In these cases, the test results are single use at the onsite location, and are not generally transferable or reusable at other settings.

Several organizations are creating onsite and point of care infrastructure necessary to support broad application of testing at locations such as airports, sporting and entertainment venues, vacation rentals, car rentals, taxis, ride share, and others.

Diagnostic manufacturers are working on home testing kits so that persons can test themselves in the privacy of their homes prior to departing for an event or series of events. In these cases, a home test could be used as part of a system to provide expedited medical care or direct distribution of pharmaceuticals like TamiFlu® in the case of influenza.

SUMMARY

An example health safety system may include a number of components or systems. For example, a vaccine system may be a component or system of a larger health safety system (HSS). The vaccine system may be function to acquire, store, and disseminate vaccination data. The HSS also may include a test system by which individuals are tested for various illnesses or diseases. That is, the HSS may be an integrated, unitary system. The test system and the vaccine system may provide test results and vaccination data to the larger HSS. Alternately, the vaccine system and the test system may exist as separate, non-related systems. The HSS may be implemented, in part, on a health safety platform. The platform and the HSS may be structured as a cloud-based system, a local system (for example, for a university). The HSS may be, may include, or may cooperate with a health safety service. The health safety service may include aspects or components of a vaccine system and a test system. Thus, the HSS may include dispersed, independent systems, services, platform, and entities that cooperate to provide the same functions and services as would an integrated, unitary system. In any implementation, the HSS may include, or may cooperate with, government and non-government organizations.

An example health safety method executed by a processor may include receiving from the test system, by the processor, a representation of biological sample data of a human sample collected from a human user and analyzed by the test system for identification of a presence of an infectious disease, and identification information identifying the user. The biological sample data includes the indication of the presence of the infectious disease; a time and date of sample collection of the biological sample; and an identification of the test system. The information identifying the identity of the user includes an attestation of the identification of the user recorded in conjunction with collecting the biological sample of the user. The method further includes registering and storing the biological sample data in a central storage; associating the attestation of the user with the biological sample of the user; and generating a certificate of association between the attestation of the user and the biological sample of the user. Generating the certificate includes analyzing the attestation of the user, based on the analysis, verifying that the collected biological sample was obtained from the identified user, and assigning a time to live for the certificate. The method then includes receiving from a venue, an access request for the user to access the venue; determining the access request is for a time within the period of the time to live; and providing the certificate of association to the venue. The health safety method also may include administration of a vaccine or inoculation and subsequent recording of vaccine or inoculation data for subsequent use in a manner that fully complies with all Federal requirements for patient privacy and protection.

In an aspect of a test method, an attestation of the user is a representation of a biometric sample of the user, the biometric sample of the user obtained in conjunction with collection of the biological sample, the representation generated by a processing device from the obtained biometric sample of the user. The biometric sample may be one or more of a thumb print set recorded from the user, a retina scan recorded from the user, and a DNA sample obtained from the user and analyzed. In a further aspect, the trusted agent may be the user. In one respect of this further aspect, the attestation is a cryptographically protected digital signature of the user.

In an aspect, the attestation is a video of the user submitting the biological sample, and the video is executed under control of a biological sample routine executed to obtain the biological sample. In a further aspect, the video is witnessed by a trusted agent and the attestation is supplied by the trusted agent. In still another aspect, the attestation is a cryptographically-encoded digital signature of the trusted agent.

An example health safety platform includes a receiving component, having a processor and a data store, that receives a test result a test of a biological sample collected from a human patient. The test result includes an indication of a presence of an infectious disease in the patient, an identification and a verification of the patient from whom the biological sample was collected, a location, time and date of sample collection, and an identification of test of the biological sample. The platform further includes a certificate component that issues a certificate of origin of the biological sample; and a data merging component that cooperates with one or more venue access managers that operate to control access to corresponding venues. The data merging component implements a distributed ledger system that stores encrypted test results of the patient and the identification and verification of the patient, and an end-to-end encryption system that receives encrypted venue access requests from a venue access manager, decrypts the access requests and determines if the access request is valid or not valid, and for valid access requests, provides an encrypted certificate of origin to the venue access manager. In an embodiment, the health safety platform may be used to detect infection from a variety of diseases, including respiratory diseases and blood-borne diseases; the platform may be used, for example, to test for infection from sexually-transmitted diseases, influenza, and COVID-19.

Another example health safety system includes a distributed computing system that in turn includes a data store, one or more processors, and wireless and wired communication equipment, the data store including non-transitory-computer-readable media storing a program of instructions that, when executed by a processor, cause the processor to receive from a test system a representation of biological sample data of a human sample collected from a human user and analyzed by the test system for identification of a presence of an infectious disease, and identification information identifying the user. The biological sample data includes the indication of the presence of the infectious disease; a time and date of sample collection of the biological sample; and an identification of the test system. The information identifying the identity of the user includes an attestation of the identification of the user obtained in conjunction with collecting the biological sample of the user. The processor further executes to store the biological sample data in the data store; associate the attestation of the user with the stored biological sample data of the user; and generate a certificate of association between the attestation of the user and the stored biological sample data of the user. To generate the certificate of association, the processor analyzes the attestation of the user, based on the analysis, verifies that the collected biological sample data were obtained from the identified user, and assigns a time to live for the certificate. The processor also receives from a venue, an access request for the user to access the venue; determines the access request is valid; and provides the certificate of association to the venue.

Another example health safety method executed by a processor of a health status provider includes receiving, by the processor, from a medical facility a certificate of vaccination for a particular disease for an individual, the vaccination conferring immunity to the individual for the disease; receiving by the processor an access request from a venue for the individual; and responding to venue access request by providing a health safety certification including the certificate of vaccination for the individual and an effective date range of the certificate of vaccination.

Yet another example health safety method includes a processor at a venue control providing requirements to allow users to access one or more venues under control of the venue control, the requirements comprising a certification of a current vaccine; the processor at the venue control receiving an access request, from a user, requesting access to a venue controlled by the venue control; the venue control requesting access to a vaccine account of the user, the vaccine account of the user maintained by a vaccine service, the vaccine account of the user comprising certified data for one or more vaccines administered to the user, the certified data obtained from medical facilities administering the vaccines; the venue control receiving authorization from the user access the vaccine account of the user the venue control accessing the vaccine account of the user; the venue control providing the venue access requirements to the vaccine service; the venue control receiving certification from the vaccine service that the venue access requirements are met for the user; the venue control notifying the user that the venue access requirements are met; and the venue control issuing the user a certified digital access document to access the venue.

A further example health safety method, implemented by a processor, includes the processor providing a list of requirements for accessing a first venue, the list consisting of one or more certifications selected from a first group consisting of a certified vaccination, a certified anti-body/antigen test result, and a certified test for absence of a virus; receiving by the processor, a request from a user to access the first venue, the request comprising a permission to acquire the one or more certifications from a health account of the user; using the permission, the processor acquiring the one or more certifications from the health account; confirming the one or more certifications conform to at least one requirement in the first group; issuing to the user a certified digital document granting access to the first venue.

A health safety system includes a non-transitory, computer-readable storage medium having encoded thereon machine instructions for implementing a health safety system and method, wherein the processor executes the machine instructions to: provide a list of requirements for accessing a first venue, the list consisting of one or more certifications selected from a first group consisting of a certified vaccination, a certified anti-body/antigen test result, and a certified test for absence of a virus; receive a request from a user to access the first venue, the request comprising a permission to acquire the one or more certifications from a health account of the user; use the permission to acquire the one or more certifications from the health account; confirm the one or more certifications conform to at least one requirement in the first group; and issue to the user a certified digital document granting access to the first venue.

A health safety system comprises a non-transitory, computer readable storage medium having encoded thereon, machine instructions, executable by a processor of a venue control, wherein the processor executes the machine instructions to provide requirements to allow users to access one or more venues under control of the venue control, the requirements comprising a certification of a current vaccine; receive an access request, from a user, requesting access to a first venue controlled by the venue control; request access to a vaccine account of the user, the vaccine account of the user maintained by a vaccine service, the vaccine account of the user comprising certified data for one or more vaccines administered to the user, the certified data obtained from medical facilities administering the vaccines; receive an authorization from the user access the vaccine account of the user; access the vaccine account of the user; provide the venue access requirements to the vaccine service; receive certification from the vaccine service that the venue access requirements are met for the user for the first venue; notify the user that the first venue access requirements are met; and issue the user a certified digital access document to access the first venue, wherein the certified digital access document is configured for storage on a smart device of the user.

DESCRIPTION OF THE DRAWINGS

The detailed description refers to the following figures in which like numerals refer to like items, and in which:

FIG. 4F illustrates a digital display rendered by a health safety application installed on a user's smart device;

FIG. 5 illustrates another example implementation of the Health Safety Systems of FIGS. 1 and 2;

DETAILED DESCRIPTION

Figure 1:
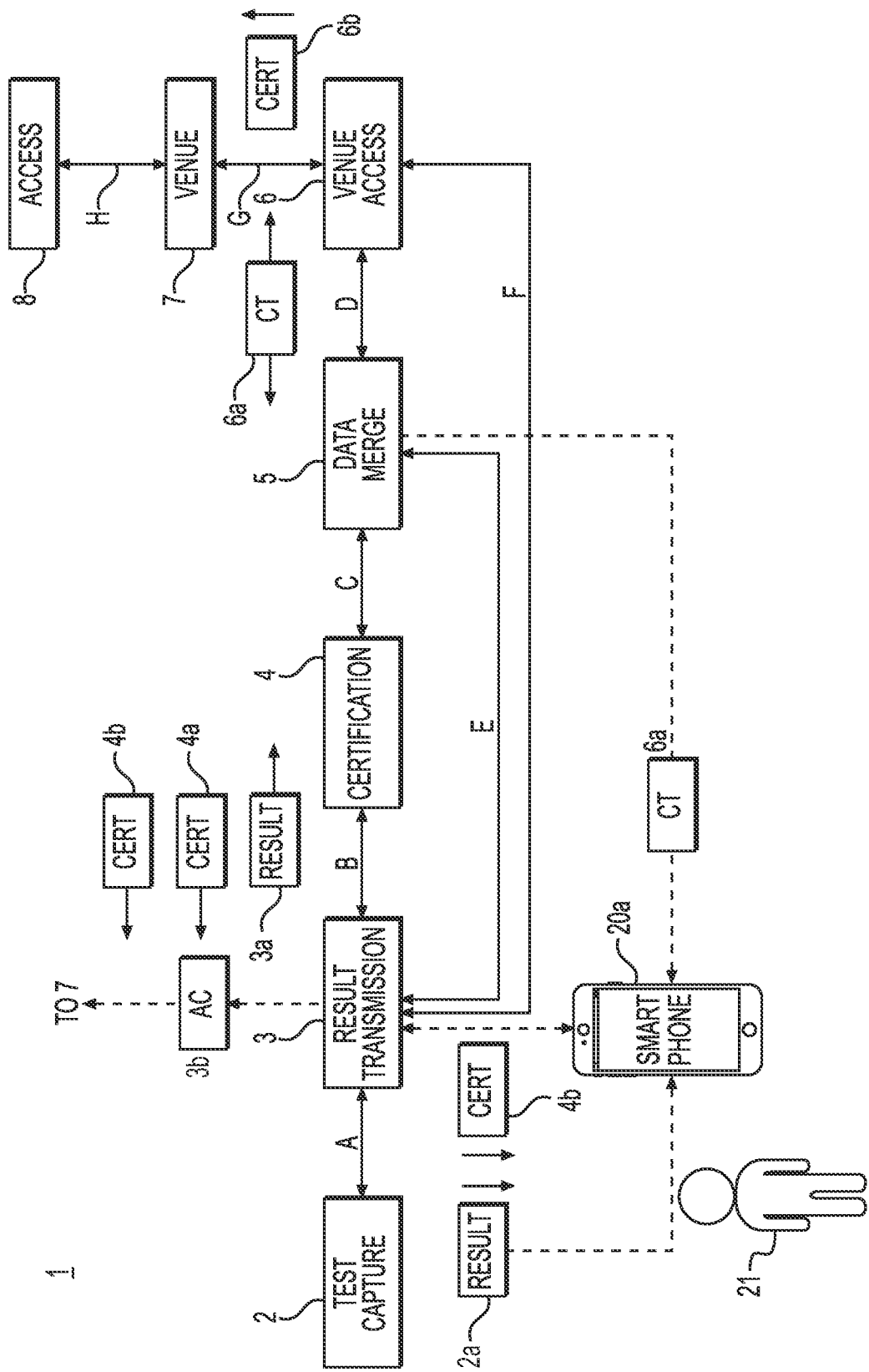
FIG. 1 illustrates an example Health Safety System.

The public health safety crises brought on COVID-19 reveals the tension between the public health interest in ensuring a venue does not pose a health risk and the privacy associated with personal health information. No current infrastructure, system, or method exists to both maintain a person's health status and provide that status in a way that ensures public health safety while protecting the person's privacy. For example, no current infrastructure, system, or method exists to maintain the status of infectious disease test results and vaccinations of a person to be tested in a way that enables the test results and vaccinations to be provided at different locations for the benefit of attendees, users, and employees (i.e., persons) without potentially violating the person's privacy. The herein disclosed systems and corresponding methods provide that privacy. Furthermore, the herein disclosed systems and methods easily adapt to changing requirements related to specific tests, vaccinations, and the varying requirements currently in place, or that may be adopted in the future, for personnel access to specific venues or venue types. Moreover, the systems and methods enable secure management of test results and vaccinations from or for the person being tested or vaccinated, and secure access to the test results and vaccination data by various parties such as an employer or an owner of a venue, all while guaranteeing the privacy of the person. For example, when a person has been tested and shown not to be infected with any single disease or with multiple infectious diseases, that disease-free status, rather than being used only once, may be used to provide access to any number of venues for a specified period of time as desired by the user and under the control of a venue owner/operator. To better ensure personal privacy, the test results and the vaccination status may be provided in a simple form that minimizes transmission of personal information. For example, the herein disclosed systems and methods may use a simple word, phrase, statement, icon or symbol to convey test results and vaccination status. More specifically, in the case of an infectious disease test result that is negative (i.e., no infection), the test result may be provided or presented to a venue operator in the form of a check mark (√), the word "negative," or the phrase "all clear." The same or a similar reporting may be used for vaccinations. Use of this reporting also reduces the burden on venue operators and others charged with verifying a person's health status prior to venue access by the person.

Testing for the presence of infectious diseases, and vaccination or inoculation (inoculation and vaccination often are used interchangeably) against infectious diseases, are at the forefront of current medical concerns. Both testing and vaccination pose several challenges. One such challenge is the need to provide timely test and vaccination results. A second, but related challenge, is protecting patient privacy. A third, and also related, challenge is to provide test and vaccination results in a manner that ensures the security, validity, and integrity of the results and data associated with testing and/or vaccination. To meet the first challenge, a current system for vaccination result dissemination is the "International Certificate of Vaccination or Prophylaxis," colloquially known as the "yellow card," issued by the World Health Organization (WHO). The hardcopy yellow card records vaccinations administered and date, and is required for entry into certain countries. However, no international standard exists for digital versions of the yellow card. Furthermore, no international standard exists for recording test results.

To meet the second challenge, and least in the United States, a current system of rules and regulation of personal information including, but not limited to health data, is protected by the Health Insurance Portability and Accountability Act (HIPPA) and the Family Educational Rights and Privacy Act (FERPA). In addition, several technological initiatives are underway to better protect information owned by healthcare providers, universities, and financial institutions. Recent changes to these laws have led to regulations affecting health records and transportability for Personal Health Information (PHI). Likewise, since the advent of COVID-19, policy discussions around concepts such as contact tracing are raising privacy concerns.

The third challenge, providing security and integrity of health sample test results and vaccination data, is being considered, but no workable solutions are available. Currently, the standard yellow cards are used; however, this record may be, and often is, subject to alteration and forgery. Furthermore, a yellow card may be lost in transit. Finally, the yellow card does not apply to some aspects of travel planning. For example, travelers to Central African nations are required to have current yellow fever vaccination, and must present the yellow card upon entry. Persons without the yellow card may be quarantined or returned to their point of origin. However, a person may purchase an airline ticket to a Central African nation without having to show a vaccination for yellow fever.

Thus, as described herein, current systems and methods for testing for infectious diseases, and preventing infection by, for example, vaccination, as well as other health safety measures, are not designed for, or capable of, providing accurate, timely, secure, and reliable reporting of verifiable infectious disease test results and vaccination status. These current systems rely primarily on paper documents that are susceptible to fraud and counterfeiting, that are cumbersome to administer, and that do not allow timely dissemination of relevant data to organizations, entities, and persons charged with ensuring health safety. A stark example of these current inefficient and outmoded systems is the International Certificate of Vaccination or Prophylaxis, or yellow card. In other words, the yellow card lacks the interoperability necessary to provide secure, tamper-proof verification of vaccinations. Even a digitized version of such a yellow card still would not provide an adequate technical solution to the COVID-19 crises. Furthermore, the current yellow card does not support a robust test result verification program. Still further, a yellow card, even a digitized version of a yellow card, is static in the sense that neither a hard copy nor a digital version can adapt to meet the time and spatially varying requirements of different venues, particularly as those venues try to comply with evolving health practices, and guidance and regulations issued by government and non-government agencies and entities. In addition, no third-party process is available for comparing yellow card status to venue access requirements. Furthermore, current systems are slow and cumbersome, and as such may lead to disregard for the health practices, or limitations on user access. For example, a cumbersome system for accessing a sporting venue may lead to pressure to change, reduce, or eliminate health safety requirements.

Disclosed herein are systems, services, platforms, and methods that provide safe and secure transmission of health safety data. The systems, services, platforms, and methods ensure validity of health data. The systems, services, and methods provide a convenient, reliable, and tamper-proof data exchange. As such the systems, services, platforms, and methods, and corresponding techniques and architectures, disclosed herein, including but not limited to receiving and using asset and/or write permissions, locking assets, instantiating assets, and/or implementing a multiple tier permission detail provide a technical solution (implementing interoperability with adequate security to avoid tampering and counterfeiting and to ensure personal privacy) to a technical problem (non-interoperability, lack of security, and lack of privacy). This technical solution improves the operation of the underlying hardware, whereby previously non-interacting hardware systems may be improved, or replaced, to provide efficient mechanisms and methods by which health care professionals and organizations, venue owners/operators, and users may interact. Furthermore, the aforementioned features provide improvements over existing health safety systems by providing a technical solution allowing greater interoperation between hardware systems as compared to existing interoperation techniques. The herein disclosed systems, services, platforms, and methods may be applied to infectious disease testing regimes as well as to vaccinations and inoculations while safeguarding a user's privacy and ensuring the security and integrity of test sample results and vaccination data. For example, as applied to vaccinations, the systems, services, platforms, and methods eliminate, or at least minimize, the possibility of forged or counterfeit vaccination documents, and provide exchange of vaccination data as may be required to access certain venues while maintaining the privacy of the exchanged data. Still further, the systems, services, platforms, and methods easily adapt to health safety requirements, as those requirements evolve over time, and vary from one geographical location to another. Finally, the systems, services, platforms, and methods are convenient to use, simple to understand, and provide expedited, but safe and secure venue access.

With the herein discloses systems, services, platforms, and methods, when a person is administered a test for an infectious disease, or receives a vaccination, at the person's request or with the person's authorization, the test results or vaccination data may be forwarded over the Internet or other communications network to a health safety service. The health safety service may confirm that the person for whom the test results have been submitted has been tested, and in the case of a positive test is eligible for and in need of available medical care, or in the case of a negative test the person may be allowed to access otherwise restricted areas or services. In the case of an antibody test, the result could also indicate immunity to a particular disease for a period of time.

In a similar fashion, a person administered a vaccine may have the vaccination data recorded with the health safety service, which in turn may cooperate with various venues to allow the person access to the venues.

A test being administered may be performed at a medical facility or point of care, at a third-party testing location (the entrance to a person's place of employment, an educational facility, an entertainment venue, a testing kiosk, etc.), or the test could be performed at home or other private location by the person themself taking the test. Vaccines typically are administered at a medical facility and possibly a pharmacy. In each case, security and privacy of the test results must be maintained. Each test, whether at a remote facility or in private setting, may have a unique test identification (ID) code. Vaccines similarly may be assigned a unique identification (ID) code. The ID code may be assigned by the test kit manufacturer, the testing facility, or the person administering the test. The test ID code or vaccine ID code may be unalterable and may be single use. The ID codes may be encrypted and written to a public ledger using a technique such as, for example, a blockchain.

For tests performed at a medical facility, point of care or third-party testing location, the test results can be verified by the person performing the test as belonging to the individual being tested. For tests done at a private location, several techniques, disclosed herein, may be used to verify that the tests results belong to the person submitting the test. Similar techniques may be used for vaccination reporting.

Private test verification/certification techniques. Tests may be verified/certified in at least the following three ways: user certified techniques; test identification techniques, and remote witness techniques. In some aspects, vaccinations may be verified/certified using similar techniques.

User certified techniques. These methods of test verification involve a user submitting some form of personal identification such as a password, fingerprint, retina scan, voice scan, facial recognition, etc., along with an attestation that they in fact are the person for whom the test results apply. The use of a password may involve two-factor authentication, as is known in the art. The password may be recoverable, if lost or forgotten, using a linked electronic device, and/or a series of challenge questions. The user also may submit a photo or video of themself taking the test along with the test results, or use other methods of identity verification. Similar certification techniques may be used with vaccinations. For example, a user may submit a form of personal identification at a vaccination site or location, and have that form of personal identification appended to a record of the vaccination.

Test identification techniques. These methods of test verification may involve collecting information from the test bio-sample itself. DNA matching, biomarker profile matching, or other techniques that are unique to person and that can be discerned by the testing system may verify the identity of the person by comparison to a sample, profile, bio-signature or other information that is on record for that person. For example, a person may create an initial bio-profile or bio-signature that is stored online or through or at a facility. The bio-profile or bio-signature then may be used for future test samples to verify the identity of the person submitting the test results. Similar techniques may be used with vaccinations.

Remote witness techniques. Tests performed in a private location may be witnessed by a third party via a video teleconference or telemedicine application. The third party may be a health care professional, a government employee, or the equivalent of a medical notary. The third party may verify that a test with a particular ID code was conducted by the person submitting the test results. The third-party certification may be merged with the test results when sent to a health status service provider.

The herein disclosed health safety system (HSS) operating on a health safety platform receives test results and vaccination data and validates/certifies that these results and data belong to a particular person. The health safety platform performs the following functions:

Maintains a user account. A user account may be established by the user, may be password protected, may have a unique ID, and may store user profile information that may include biometric markers, signatures or other identifiers. The unique ID also may be employed to ensure greater user anonymity and privacy, as disclosed herein.

Receives a test result from a user. Test results may be sent from a point of care facility, a third-party testing facility, or a home test system to a health status provider. Information may be sent and received in an encrypted format and/or may be protected with blockchain techniques to ensure complete privacy of the user's information. To further ensure privacy, a user may be anonymized such that the user's name and image are not stored in the health safety system, and instead, a reference known only to the user is employed to link the user to the user's information. Similar privacy measures may be invoked for vaccinations.

Maintains a secure copy of the user's test results and vaccinations.

Establishes a timestamp for the test results. Some test results, such as those from antigen tests are testing for active infection and may only be valid for a defined period. Other test types, such as antibody tests, may show long-term immunity to an infection and may be valid for months or years. As a result, the health safety platform may establish a timestamp for the test results. Some vaccines may not become effective for a defined and known period after administration. Thus, vaccine data certifications may specify an effective start data that is subsequent to the date of vaccine administration. Additionally, for some infectious diseases, the efficacy of the vaccination may need to be proved by a subsequent antibody test. This antibody test may follow the procedures and use the techniques noted herein for testing for the presence of the related infectious disease. Furthermore, some vaccinations may be required periodically to maintain immunity. Thus, a vaccination end date also may be specified.

Establishes a quality of certification of the test results. Based on the various ways that a test can be certified, the HSS may assign a measure of certainty that the test results belong to the person submitting the test results. For example, in the lowest level of certification the user submitting the results attests that these results belong to them. This is the lowest level of certification because users could submit unverified or false information that the test results actually belonged to them. In the highest level of certification, a DNA signature could be matched to validate that the test results belong to the user. Various levels of certification can be established in between, where third parties validate the test results as belonging to the user.

Provides test results, test type, timestamp and level of certification to third parties with the user's permission. In some cases, the level of certification is not required.

Logs all interactions where health status was provided to third parties and user authorizations. This information may be used to provide a health history over time for the user.

FIG. 1 represents a general approach that may be applied to infectious disease testing. The same or similar approaches systems, services, platforms, and methods may be applied to vaccinations, providing the same or similar mechanisms for receiving, processing, storing, and providing data related to the vaccinations while safeguarding a user's privacy and ensuring the security and integrity of the vaccination data.

In FIG. 1, health safety system 1 includes a test capture and analysis component 2, a health status result transmission component 3, a certification component 4, a data merging component 5, and a venue access component 6. In an embodiment, the test capture component 2 and the transmission component 3 communicate over interface A to cooperatively allow administration of a health test of user 21, analysis of the test, and generation of a test result by the test capture and analysis components 2. The component 2 may supply the results of a test to the component 3 over the interface A. In an aspect, the test capture and analysis component 2 and the transmission component 3 may be combined in a single hardware device. In another aspect, the components 2 and 3 may be stand-alone hardware devices. In an aspect, some functions of the transmission component 3 may be embodied in another component, such as a smart device, including smart phone 20a or a similar device, for example.

In an embodiment, the test capture and analysis component 2 may be implemented at a kiosk. The kiosk may be located at a specific venue, such as at the entrance to a theme park, a stadium, or an airport terminal. Alternately, the kiosk could be located at a business entrance, and may be used by employees of the business and visitors to the business. Alternately, the kiosk could be located at a pharmacy or at a medical clinic. In this embodiment, the kiosk also may provide some or all the functions of the transmission component 3.

In an embodiment, the test capture and analysis component 2 is, or includes a specific health test kit, such as a test kit for testing user 21 for possible infection from COVID-19 or other relevant diseases potentially affecting public health. Such a test kit may be a small, portable device configured to cooperate with the transmission component 3. The test kit may include mechanisms, such as swabs, to acquire a sample from user 21, analyze the sample, and provide test result 2a to the transmission component 3 over the interface A.

In an embodiment, user 21 may employ the test kit to self-perform a health test, such as when at home or other private setting.

In another embodiment, such as when implemented at a kiosk, the test capture and analysis component 2 may be configured to perform different types of health tests, such as for COVID-19, influenza, and/or other relevant diseases potentially affecting public health.

The health status transmission component 3 may include mechanisms to control operation of the test capture and analysis component 2. For example, when implemented in the smart phone 20a, the component 3 may include or be in communication with an application (not shown) of the smart phone 20a, and the application may initiate analysis by the component 2, may provide data related to the user to the component 2, and may provide security for the test result 2a (e.g., encryption). Such security processes, and associated security mechanisms are described in more detail herein. Following any processing at the component 3, the test result 2a and any associated data may be sent, encrypted, or otherwise protected, as secure test result 3a to the certification component 4.

The certificate component 4 receives the secure test result 3a over interface B from the health status transmission component 3. In an aspect, the components 3 and 4 may be combined into a single unit or single hardware device. In another aspect, the components 3 and 4 may be co-located such as at a medical clinic. In yet another aspect, the components 3 and 4 are separated and may communicate over a wireless communications network. The transmission mechanism, when components 3 and 4 are not combined in a single unit, may include any suitable digital data exchange mechanism. A process of secure test result 3a transmission is described in more detail herein.

In an embodiment, the certificate component 4 functions to process a secure test result 3a, and from the test result processing, generate a digital document such as digital certificate 4a attesting to the acceptability of the test result for one or more purposes. Those purposes may include, for example, allowing the user 21 whose health is represented by the digital certificate 4a to access one or more venues that are associated with venue access component 6. The digital certificate 4a also may include the test result as well as all information provided in the secure test result 3a. The digital certificate 4a may include the date and time of sample collection, the test kit identification, including manufacturer and date of manufacture, test type, and a unique serial number, or other identification, of the test kit. The digital certificate 4a further may include a time to live for the test result; the time to live may be a date or period of time, agreed upon by medical personnel, such as, for example, 24 hours, one week, etc., beyond which the test results no longer will be accepted for venue access. Upon reaching the time to live, the digital certificate 4a may be disabled, deleted, and/or flushed from any existing storage in the system 1. Alternately, the digital certificate may simply be permanently disabled or deactivated such that it no longer may be used in the system 1 to allow user 21 to gain access to a venue. The digital certificate 4a may include an effective start date. An effective start date may be used for vaccinations, for example. The digital certificate 4a also may include a quality value. The quality value may be based on the type of test and the identity of the test kit. The quality value further may be based on the process or modality by which the sample is collected and the test result is produced from the sample. The quality value still further may be based on the degree of security, or confidence, in the reliability of the test result. In this regard, a sample collection and analysis modality that provides as close as possible to absolute verification that the user 21 submitting the sample is in fact the user sampled may produce a highest quality value. For example, a test sample collected by a medical professional at a medical clinic and processed to produce a test result by the medical professional may have a highest value. A test sample collected at a kiosk and analyzed at the kiosk may have a high value. A test sample collected by user 21 and applied to a home test kit may have a medium value. Other quality factors and quality rating systems may be employed. A digital certificate 4a with a highest quality may allow user 21 access to any venue while a digital certificate 4a with a medium quality value may allow access to certain venues but not others. In an embodiment, the user 21 may be provided with the quality value required by a venue and the quality value a specific test sample collection and analysis modality will produce, thereby allowing the user 21 to select a modality that should produce the required or desired quality value. In an aspect, the digital certificate 4a may be used to access a specific venue, or a number of related venues, and may be used for a single access or a limited number of accesses. In another aspect, the digital certificate 4a may be used to access any venue that recognizes or accepts use of the digital certificate 4a, and such access to any venue may apply for a time limited by the validity of the digital certificate 4a.

In an embodiment, for test results, the certificate component 4 may provide the digital certificate 4a to the component submitting the secure test result 3a. For example, if the submitting component is the smart phone 20a of user 21, the certificate component 4 may transmit the digital certificate 4a to the smart phone 20a. If the test result submitting component is a kiosk, the certificate component 4 may provide the digital certificate 4a to an address input to the kiosk by the user 21; for example, an email address of the user 21. Alternately, the certificate component 4 may provide the digital certificate 4a for printing at the kiosk. When printed, the printed digital certificate 4a may include as a digital object, a tamper-proof RFID (e.g., a read-once RFID) or other digital object such as a two- or three-dimension bar code. In any aspect, the digital certificate 4a may include an indication readable by the user 21 as to the quality value (e.g., highest, high, medium). A similar process may be used for vaccinations.

In another embodiment, the certificate component 4 produces a digital certificate 4b with a tamper-proof reference. The reference then may be used to look up and retrieve data such as that incorporated in the digital certificate 4a. The user 21 may employ the digital certificate 4b in its digital form or in a printed form. For example, the user 21 may provide the digital certificate 4b on the user's smart phone display, where the digital certificate may be read at a venue access point.

In an embodiment, the certificate component 4, or aspects of the certificate component 4, may be implemented in a cloud-based system. For example, the component 4 may maintain active as well as deactivated digital certificates 4a, 4b in a cloud storage facility. The digital certificates may be stored using techniques of a distributed ledger, including blockchain techniques.

In an aspect, to provide security and privacy for the user 21, the digital certificates 4a and 4b may be anonymized such that the components 4/5 maintain only a unique identification of the user 21 (for example, a user account number with the components 4/5), and does not maintain the user's name or image data. The user identification may be encoded in a two- or three-dimensional bar code, or another appropriate digital object, for example. The components 4/5 maintain the user's account based on the user ID, and the user 21 maintains a copy of the digital object on smart phone 20*a*. The digital object is scannable, and may be scanned at a venue point of entry, and may be provided to venue access component 6. Venue access component 6 may in turn provide the digital object to a venue 7, which may use the digital object to correlate to a test or vaccination certificate maintained on the user's smart phone 20*a*. Alternately, or in addition, venue access component 6 may provide the digital object to the components 4/5 to obtain the user's health status, and may provide the health status to the venue 7. These transactions of the system 1 thus may be executed without risk to the user's privacy or security. Additionally, the transactions may be end-to-end encrypted, may employ a distributed ledger, and further may employ a permissioned or permission-less block chain architecture, as disclosed herein.

As noted herein, the components 3 and 4 may be combined on a single hardware device. In an embodiment, the certificate component 4 may be implemented on the smart phone 20*a* (or another smart device operated by the user 21, such as a tablet or computer). In this embodiment, digital certificates 4*a* are stored on the smart phone 20*a*, where they remain active until expiration of the assigned time to live, or other criteria. When implemented on the smart phone 20*a*, the component 4 may be a component of the application 22. When implemented on a computer, the component 4 may be a component of a non-transitory computer-readable medium storing a program of instructions (not shown in FIG. 1).

When implemented as a service separate from the health status transmission component 3 (e.g., as a cloud-based service), the certificate component 4 may transmit the digital certificates 4*a*, 4*b* to the data merging component 5 over interface C. In an aspect, such transmission may require authorization from the user 21. In another embodiment, the user 21 may operate the smart phone 20*a*, or other smart device, to transmit the digital certificates 4*a*, 4*b* to the data merging component 5 over interface E.

The data merging component 5 may produce a certified ticket 6*a* that the user 21 may employ to access a specific venue 7. However, the certified ticket 6*a* need not be a "ticket" in its common use. For example, when user 21 employs the HSS 1 to schedule a ride-sharing service, the "certified ticket 6*a*" may be, instead, an electronic file or other mechanism appropriate for a ride sharing service. The data merging component 5 may produce the certified ticket 6*a* by merging a satisfactory certification 6*b* from the venue access component 6 with a digital certificate 4*a*, having acquired the digital certificate 4*a* from the certificate component 4 or the health status transmission component 3. The data merging component 5 may generate the certified ticket 6*a* when requested or authorized to so by the component 3.

The venue access component 6 may communicate directly with the health status transmission component 3 over interface F and/or with the data merging component 5 over interface D. The venue access component 6 may communicate with one or more venues 7, each of which may control one or more venue access points 8. In an aspect, a venue access point is a gate or entry to a venue 7. The venue access point 8 may be provided with an access control device including, but not limited to a processor-controlled turnstile. The access control point 8 may be configured to allow user 21 to access the venue 7 based on satisfactory reading to a certified ticket 6*a* independent of how the certificate is read or how access is controlled. The access point 8 may be manned, or may be an autonomous device; i.e., a device that operates without human control or interaction except for interactions with user 21.

In an embodiment, the venue access component 6 may be a component of a venue 7 and further may be implemented at a venue access point 8. In another embodiment, the venue access component 6 acts as a control service for multiple venues 7, none of which need be related to each other. For example, one venue 7 could be an airport and a second venue 7 could be a theater.

In an embodiment, the certified ticket 6*a* may be produced by the venue access component 6 based on inputs received from the test result, or health status transmission component 3 and/or the data merging component 5. In an aspect, the component 3 may provide a digital certificate 4*a* to the venue access component 6. In another aspect, the component 3 may provide the venue access component 6 with authorization and a mechanism to acquire a digital certificate 4*a* from the data merging component 5. In yet another aspect, the component 3 may provide the venue access component 6 with authorization and a mechanism to acquire a certified ticket 6*a* from the data merging component 5.

In the aspect in which the transmission component 3 provides the venue access component 6 with authorization and a mechanism to acquire a digital certificate 4*a* from the data merging component 5, the venue access component 6 may generate the certified ticket 6*a*.

The health status transmission component 3 may communicate directly with a venue 7 to request access to the venue 7; that is, to buy a ticket from the venue 7 so as to allow the user 21 to enter the venue 7. Access request 3*b* may include an implicit or explicit authorization from user 21 to release the user's digital certificate 4*a*. Alternately, the access request 3*b* may include the digital certificate 4*a*. The venue 7 may pass that access request 3*a* to the venue access component 6, which may in turn pass the access request to the data merging component 5.

In an embodiment, the processes executed by the components 5 and 6 may result in a user device such as smart phone 20*a* being provided with a certified ticket 6*a*. Alternately, the certified ticket 6*a* may be provided to the venue 7 for pickup by the user 21. In this alternative, the certified ticket 6*a* may be in digital form (i.e., the certified ticket 6*a*) or may be printed at the venue 7 and acquired thereat by the user 21 (e.g., will call), when the user 21 supplies the venue 7 with a satisfactory certification 6*b*, which may be a separate digital file. A satisfactory certification 6*b* is described in more detail herein.

Figure 2:
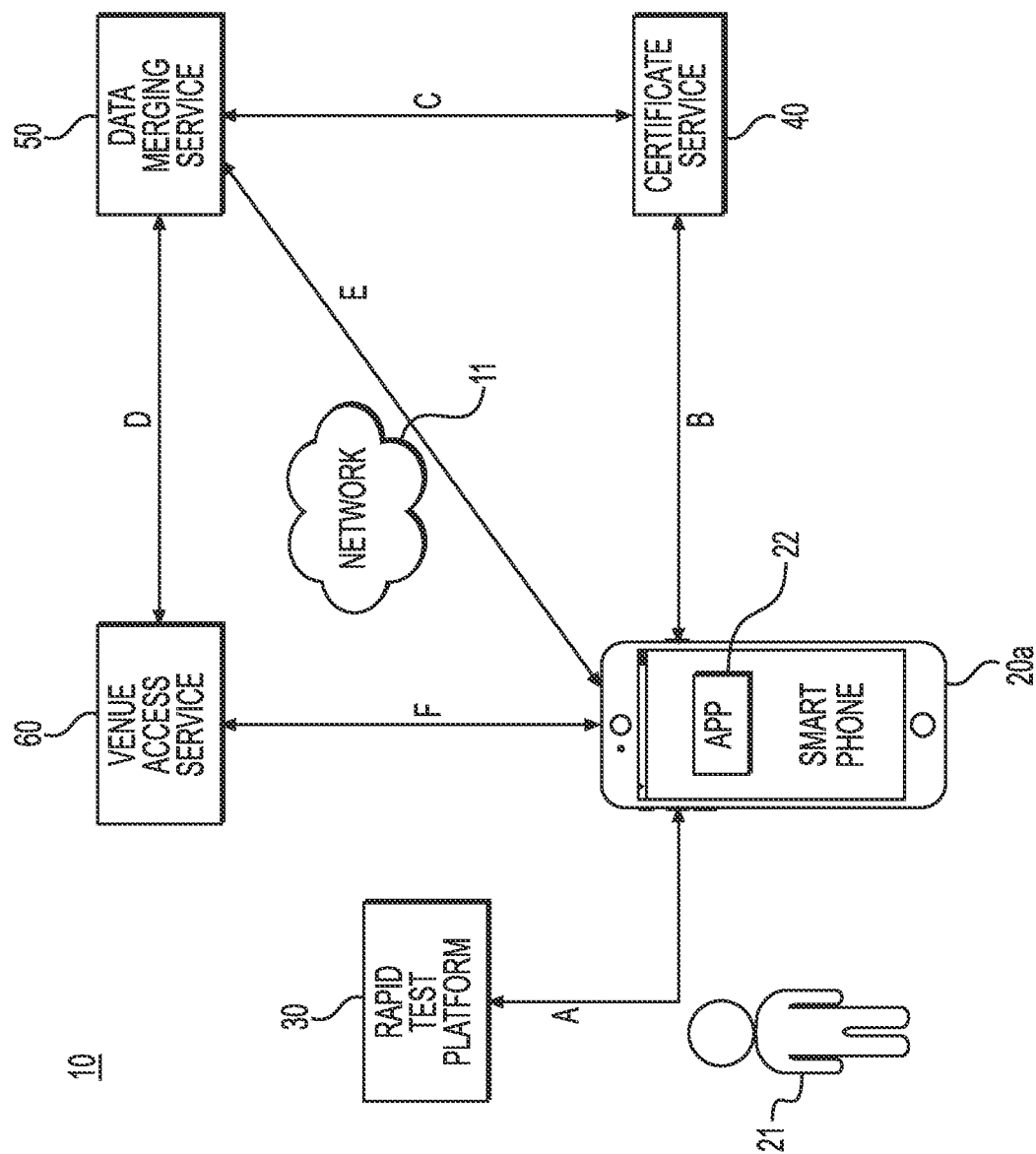
FIG. 2 illustrates another example Health Safety System.

FIG. 2 illustrates an embodiment of a Health Status System (HSS) that executes aspects of the system of FIG. 1. The HSS embodiment of FIG. 2 may be executed in part at a home of user 21, or at another private location of user 21, such as at a hotel room. Thus, in one aspect of this embodiment, user 21 may not interact directly or indirectly with any authenticating authority such as a medical professional, a notary, or other person. In a second aspect, user 21 may interact with such an authenticating authority.

In FIG. 2, Health Safety System (HSS) 10 includes a personal device 20 operable by user 21. The personal device 20 may be used in conjunction with rapid test platform 30. The HSS 10 further includes certificate service 40, data merging service 50, and venue access service 60. These and other components of the HSS 10 may communicate over communications network 11.

In an aspect, the personal device 20 may be a smart device. Such a smart device may include a program of instructions executed by a smart device processor to support operations of the HSS 10. Alternately, the smart device may include an HSS application 22 that functions to support operations of the HSS 10. The smart device may be a smart phone, tablet, or computer, for example. In another aspect, the personal device 20 may be a dedicated device. Such a dedicated device may include a program of instructions that are executed by a processor on the dedicated device to support operations of the HSS 10. Alternately, such a dedicated device may include an application specific integrated circuit (ASIC) programmed to support operations of the HSS 10. The personal device 20 may be capable of wired and wireless communication, including Bluetooth® communication, with other devices or components of the HSS 10, and devices and components outside the HSS 10. In an aspect, the personal device 20 is smart phone 20a.

Wired communications among entities in the HSS 10 may occur over a public network such as A PSTN and/or over a dedicated wired network. A dedicated wired network may be a secure wired network. Wireless communications may occur over a wireless communication network 11, which may be a wide area network (i.e., the Internet) separated from the HSS 10, and/or over a local area network (LAN), which may be implemented by components of the HSS 10. The communications network 11 may be or may include a virtual private network (VPN) implemented separately from the HSS 10 or as an adjunct to the HSS 10.

The HSS 10 may include one or more rapid test platforms 30. As disclosed herein, such test platforms 30 may be dispersed throughout the HSS 10. The test platforms 30 may be capable of wired communications and wireless communications. Operation of the test platforms 30 is described in more detail herein. However, as shown in FIG. 2, a test platform 30 may be in wired or wireless communication, including Bluetooth®, with personal device 20. In operation, a test platform 30 may be in close proximity to the personal device 20; that is, for example, within a few feet of the personal device 20, such as within 12 feet. In an aspect, the personal device 20 may include a camera (not shown in FIG. 2) that is used as an element of the operation of the HSS 10, where the camera provides a view of the test platform 30, which is made possible by such close proximity.

In an aspect, a test platform 30 is a one-time use device. The platform 30 may be battery powered. The platform 30 may be implemented to perform a specific test or to perform one or more similar tests. For example, a test platform 30 may be implemented to test for influenza, to test for COVID-19, or to test for both. The test platform 30 includes all components needed to execute a test, such as a test for COVID-19, and to provide the results of the test to the personal device 20.

In another aspect, the test platform 30 may be capable of multiple uses. In a respect, the test platform 30 may be capable of multiple uses by a same user 21. In another respect, the test platform 30 may be capable of use by multiple users 21.

In addition to providing the test result to the personal device 20, the test platform 30 may provide a unique identification. In an aspect, the unique identification may provide one or more of a unique test platform serial number, an identification of the test (e.g., for COVID-19, including the specific test type), test platform manufacturer and date of manufacture (e.g., in case of a shelf-life), and date and time of test. In an aspect, the test platform 30 may provide the geographic location of the test platform. In a respect, the test platform 30 may query the personal device 20 to obtain the geographic location. In another respect, the test platform 30 may obtain the geographic position from an existing but separate GPS system.

When the test platform 30 is used for multiple tests, the test platform 30 may employ a counter, and may provide the counter value with the unique identification.

The test platform 30 may interface with an application 22 implemented on the personal device 20. The application 22 may be acquired from an online store, for example, and may be intended for use with the specific test platform 30.

In an aspect, the application 22 may implement security measures to first verify the validity of the test, second protect the test result from corruption, hacking, or other attack, and third preserve the privacy of the user 21. For example, the application 22 may implement an end-to-end encryption routine. Such security measures are described in more detail herein. The application 22 also may present the test results (or a summary of the test results) for display to the user 21 on a screen or other graphical user interface of the personal device 20.

The personal device 20 may communicate directly with each of the services 40, 50, and 60 in a manner similar to communications described with respect to FIG. 1, and for the same or similar purposes. Thus, operations of the HSS 10 may result in the user 21 acquiring a certified ticket (similar to certified ticket 6a of FIG. 1). In this first aspect of the embodiment of FIG. 2, such certification may be based on one or more actions taken by the user 21. In one action, the user 21 digitally signs an affidavit that it was the user 21 whose sample was taken and tested. A false attestation may result in civil or criminal penalties. The user 21 may submit a biometric sample with the test sample. The biometric sample could be a retina scan or thumbprints, for example. Other biometric samples may be submitted. At a venue point of entry, the user 21 would submit the same biometric sample type to confirm the user's identity. Alternatively, the HSS 10 could submit to the venue not only the test certificate for the user 21, but also the biometric signature of the user 21. In one action, the user 21 could submit thumbprints at a turnstile or point of entry, and the certificate service 40, or other component of the HSS 10, would then immediately send the certificate from the user 21 along with validity of the user's biometric signature, allowing fast and immediate access for the user 21. A thumbprint sample collection process may be implemented in the application 22, for example, using a thumbprint collection window displayed on a screen to the smart phone 20a. In a further aspect, the personal device 20, equipped with a camera, may capture an image of the user 21 when the thumbprints are collected. The application 22 then would execute to cause the personal device 20 to transmit the thumbprints and the image, along with the test results, to the certificate service 40.

Figure 3:
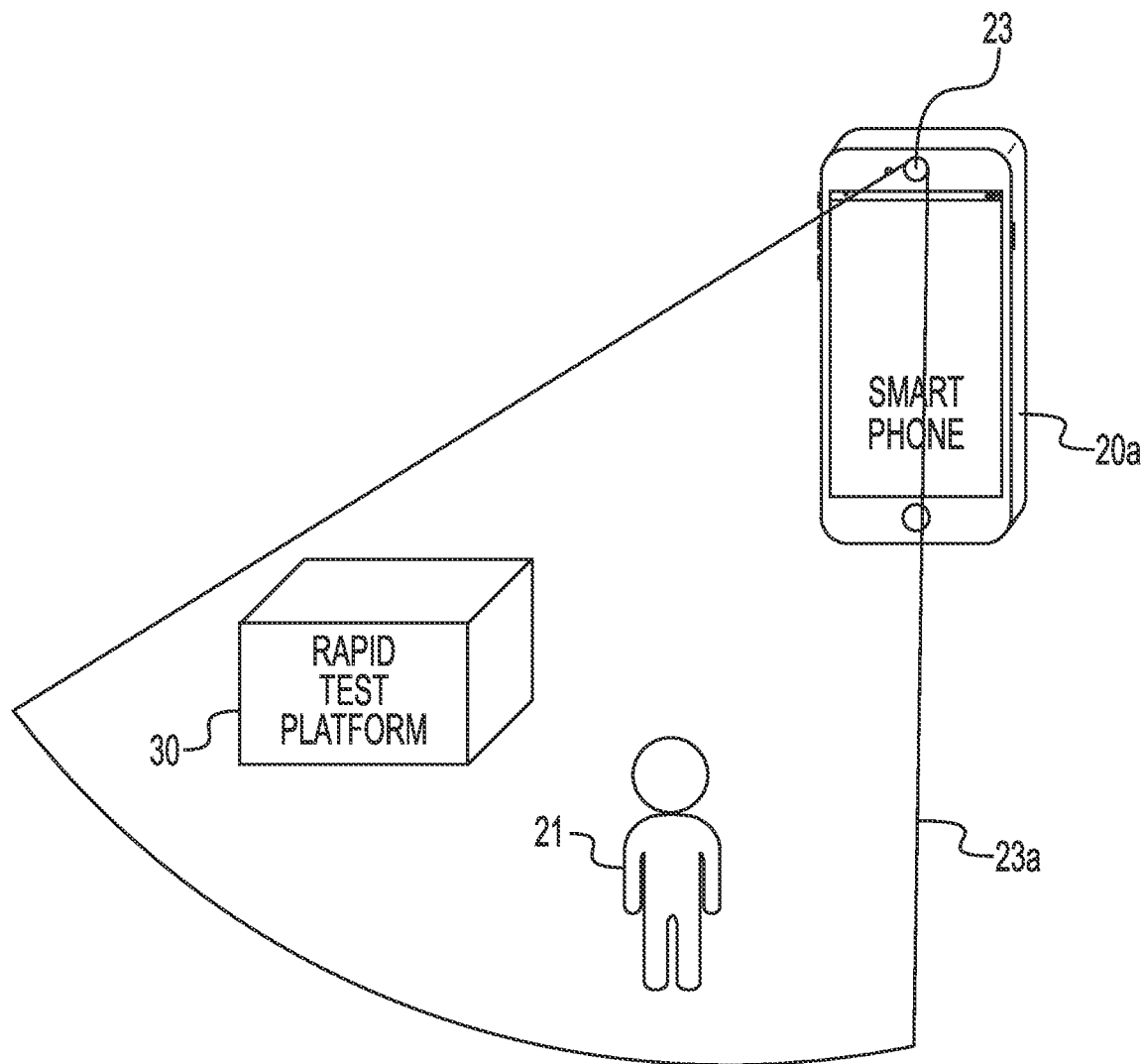
FIG. 3 illustrates a sample validation operation executed by components associated with the example Health Safety Systems of FIGS. 1 and 2.

The second aspect of the embodiment of the HSS 10 may incorporate additional authentication elements, as shown in FIG. 3. In FIG. 3, the user 21 is instructed to arrange the test kit 30 and the smart phone 20a so that the camera 23, with field of view 23a, may capture still frames or a video to record the sample collection. The recorded images then are included with the test results sent to the certificate service 40.

Figure 4A:
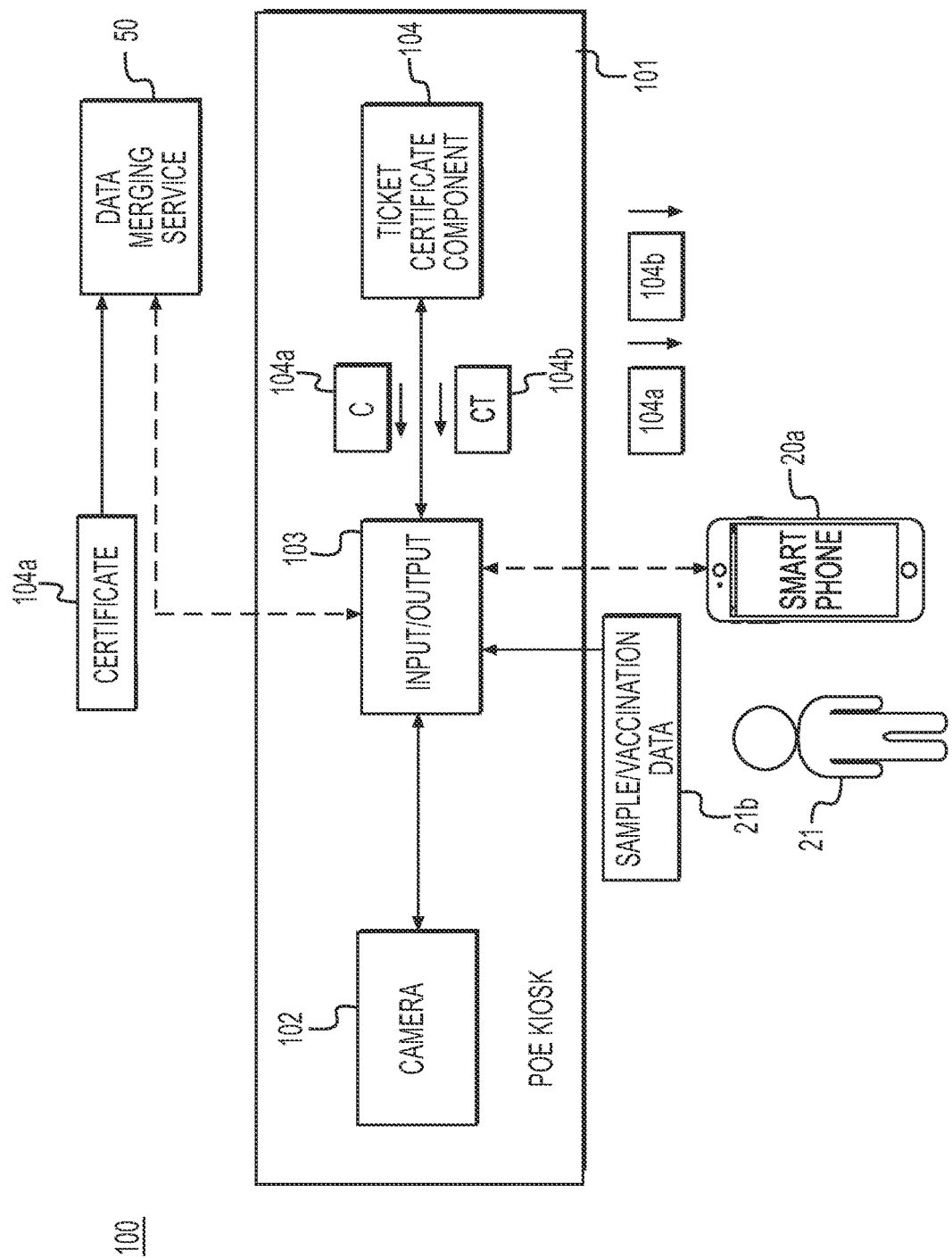
FIG. 4A illustrates an example implementation of components of the Health Safety Systems of FIGS. 1 and 2.

In an embodiment, an HSS may be implemented in part at a point of entry (POE) kiosk for a specific venue such as an airport, a stadium, a theatre, or an office building. FIG. 4A shows HSS 100 implemented at POE kiosk 101. The kiosk 101 includes camera 102, input and output test device 103, and ticket certificate component 104. In an aspect, user 21 accesses test device 103 to access a sample collection instrument such as a swab (packaged in a sanitary container), uses the swab to collect a sample, and then inserts the swab in a collection port, at which time, the test device 103 reads and analyzes the collected and submitted sample. After analysis is complete, the test device 103 notifies the user 21 through a display that the test result in negative (good) or positive (not good). For negative test results, the test device 103 communicates the results to the certification component 104. The certification component 104 generates a certificate 104a, which the user may combine with an existing ticket to allow access to the venue associated with the POE kiosk 101. Alternately, such as when the user 21 does not have an existing ticket, the certification component 104 may generate a certified ticket 104b that may be used to access the venue. Generating the certificate 104a may require payment of a fee. Generating a certified ticket 104b also may include the base cost of ticket. In some aspects, the certificate 104a may not require payment of a separate fee.

Similar to use for POE testing, a venue access point may include a POE vaccination station, manned by appropriate medical personnel, who may administer vaccinations to users who cannot offer proof of vaccination. Such a POE vaccination station could be established at a departure point of an international airport, and could allow arriving passengers who lack proof of vaccination to obtain vaccinations required for entry. In addition to the vaccination, the POE vaccination station may upload certified vaccination data to a user's vaccine account, and such data could be used for subsequent venue accesses that require a certified vaccination.

Either the certificate 104a or the certified ticket 104b could be printed or could be provided to the user's smart phone 20a. The camera 102 my record the sample submission and provide a still image of the user 21 on the certificate 104a or the certified ticket 104b. The certificate 104a and the certified ticket 104b may come with an expiration date, or more broadly, a time to live, after which the user 21 may not be able to access the venue (for example, a venue owner/operator may establish a cut-off date that is earlier than a stated expiration date, or less than a stated validity period). Similar techniques may be used for vaccinations, and a corresponding certificate 104a or certified ticket 104b may reflect an expiration date or time to live. For example, a cruise operator may establish a time to live for a COVID-19 vaccination that is 30 days less than a stated vaccination expiration date.

In an aspect, the HSS 100 may provide a certificate 104a to a data merging service 50, where the certificate 104a may be used, within its time to live, to access other activities at the venue, or to access other venues controlled by a same venue owner/operator. However, one implementation is that the assigned time to live would expire at the end of the specific event at the venue to which the user 21 requests access, or shortly thereafter.

Figure 4B:
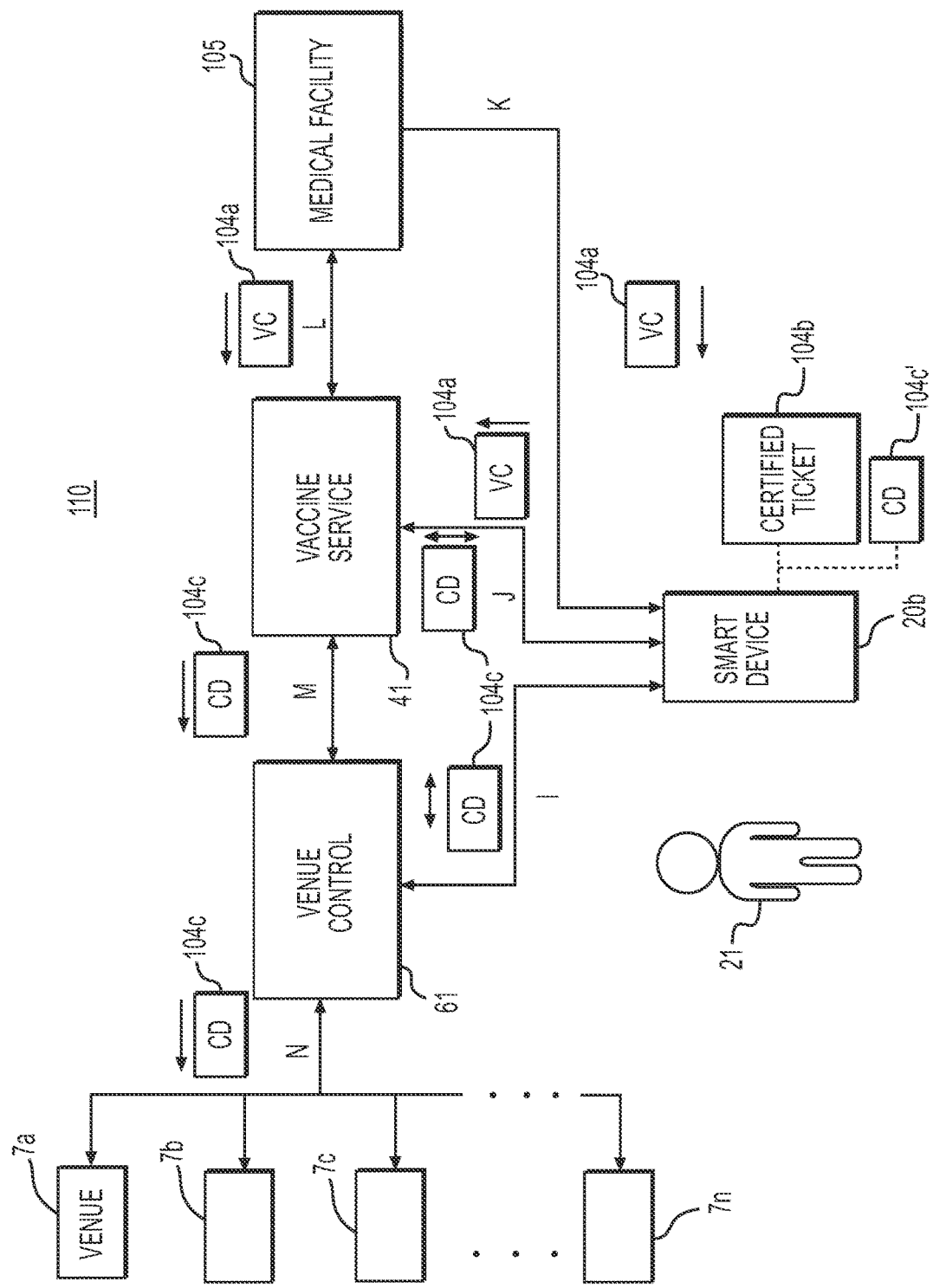
FIG. 4B illustrates another example implementation of components of the Health Safety Systems of FIGS. 1 and 2.

FIG. 4B illustrates another example health safety system. In FIG. 4B, health safety system 110 provides health safety status information for users, such as user 21, and operates to provide safe access by user 21 to venues 7a-7n, which may operate under control of venue control 61 (venue control 61 may be implemented by a venue owner/operator). Safe access may be based on valid, accurate, and verifiable test sample results, including antibody tests and antigen tests. Safe access also may be based on current and verifiable vaccinations. Finally, safe access may be based on both valid, accurate, and verifiable test sample results and current and verifiable vaccinations. The system 110 is described with respect to specific systems or subsystems, components, modules, hardware devices, and data objects, some of which may be part of an integral health safety system, and others of which may cooperate and communicate with the health safety system. In one aspect, health safety system 110 includes vaccine service 41. In another aspect, health safety system 110 includes venue control 61. In yet another aspect, health safety system 110 includes both vaccine service 41 and venue control 61. Other combinations of components of FIG. 4B are possible. Furthermore, vaccine service 41 may provide the same functions as the components 2-5 of FIG. 1, and venue control 61 may perform the same functions as venue access 6 of FIG. 1. As shown, medical facility 105 may perform vaccinations of users such as user 21. In an aspect, the medical facility 105 may provide a digital certificate, such as vaccine certificate 104a attesting to the vaccination, to a designated smart device 20b of user 21 over path K and/or to vaccine service 41 over path L. Vaccine service 41 may store the vaccine certificate 104a in an account of user 21, where the account is maintained at the vaccine service 41. The smart device 20b also may store the vaccine certificate 104a. The vaccine certificate 104a may be encrypted for transmission. The vaccine service 41 may combine the vaccine certificate 104a with other information and data, such as biometric data of the user 21, to create a digital certified access document 104c (which is similar to a certified ticket 104b). The vaccine service 41 may provide the digital certified access document 104c over path J on demand from the user 21 operating smart device 20b. The vaccine service 41 also may provide the certified access document 104c over path M to the venue control 61. Alternately, the smart device 20b may provide the digital certified access document 104c over path I to the venue control 61 in order for the user 21 to access one or more of the venues 7a-7n. In another alternative, the smart device 20b may store only test sample results and vaccination data, without linking the test sample results and vaccination data to other personal information of user 21. In yet another alternative, once a digital certified access document 104c has been scanned a configurable number of times, the document 104c may be deleted without action of user 21. Furthermore, if a test sample result or vaccination has expired, the document 104c may be deleted (and user 21 may be so notified) from storage on smart device 20b or at vaccine service 41.

The venue control 61 communicates with venues 7a-7n over path N, and may provide one or more of the venues 7a-7n with the digital certified access document 104c. At a specific venue, such as venue 7a, the user 21 may present identifying information that may be scanned at a point of entry (venue access point) to venue 7a, and venue 7a may confirm access authorization by comparing the identifying information with corresponding information contained in the digital certified access document 104c. Alternately, user 21 may simply have the local copy of digital certified access document 104c, which would be resident on smart device 20b, scanned at the point of entry of venue 7a. Alternately, user 21 may generate a printed copy 104c' of the digital certified access document 104c, and use the printed copy 104c' to access venue 7a.

In the health safety system 110 of FIG. 4B, user 21 is shown with smart device 20b. In general, a smart device can connect to other devices over networks, typically using a wireless protocol, and can operate to some extent both interactively and autonomously. Thus, smart device 20b may be any computing platform capable of processing and displaying data that enables the transfer of information and data necessary for safe venue access. For example, smart device 20b may be a smart phone, a smart watch, a tablet, or a computer. Devices other than smart device 20b may be used with health safety system 110. Such other devices may be configured as small, lightweight, and disposable devices, and may incorporate RFID technology, for example. As such, the RFID device may incorporate either active or passive RFID components, which include a microchip, a receive/transmit antenna, and for active RFID devices, a power supply (e.g., a battery). Such RFID components are well known in the art. As contemplated herein, such RFID devices may be purpose-built for a particular application, and will be referred hereinafter as RFID devices, to distinguish RFID devices from typically more capable smart devices, such as a smart phone. Nonetheless, in an aspect, some capabilities and functions of smart device 20b may be incorporated into an RFID device such that the RFID device may store test results and vaccination data and status for user 21. A wearable RFID device may be a disposable wrist band (e.g., a stretchable rubber bracelet), necklace, or pendant that has encoded on it identifying information of user 21, and optionally the current test results and vaccination status of user 21. The user information, optionally including biometric data such as a thumbprint; a photograph; a digital facial mapping; user account information; and test result and vaccination status, may be encoded in an RFID device embedded in the wrist band. When the RFID device is read at a venue access point, some or all of the information may be displayed to venue access control personnel to confirm safe entry. Alternately, only a simple check mark, or similar indicator, as disclosed herein, may be displayed. As another alternative, the RFID device may be read at an automated venue access point by appropriate RFID equipment, which then may retrieve from the RFID device, user identification information. The retrieved user information may be, for example, a digital facial mapping that may be compared through use of facial recognition techniques, to the user wearing the RFID device. As yet another alternative, the venue access point RFID equipment may simply obtain a code from the RFID device, and the venue access point RFID equipment may use the code to query a cloud-based repository (operated and maintained by, for example, venue control 61 or vaccine service 41), to determine the test results and vaccination status of user 21 as pertains to the specific venue that user 21 is seeking to access. In an aspect, the venue access point RFID equipment may query and obtain only those test results and vaccination status information that the venue control 61 establishes for the specific venue. For example, venue 7a may require proof of a current COVID-19 vaccination, but user 21 may have a health safety account with either venue control 61 or vaccine service 41, with the health safety account recording test results for various infectious diseases and recording vaccination data for diseases in addition to COVID-19. Because venue 7a requires only a current COVID-19 vaccination, only that COVID-19 vaccination information, and no other medical information from the health safety account of user 21, is presented at the venue access point for venue 7a. Furthermore, the COVID-19 vaccination information may be indicated at the venue 7a access point as a simple check mark (√). In an aspect, user 21 may be issued a disposable wrist band by venue control 61 (for example, by mail or for pick up at venue 7a), and the encoded information thereon may be provided by vaccine service 41 or from the user's smart device 20b. When provided at the venue 7a, the disposable wrist band may already be encoded by the venue control 61. Alternately, the encoding may occur at the venue 7a by operation of application 22 on the user's smart device 20b transmitting the required certifications (for testing and vaccinations) to encoding equipment operating a venue access point for venue 7a. A cruise line operator, as a venue control, may issue the wrist band to user 21, and user 21 may employ the wrist band on board ship, to access ship venues, to disembark at ports of call, and at the ports of call, to tour local sights and attractions. Still more specifically, the cruise line operator may contract with local authorities in a port of call and local museums and other attractions at the port of call, and user 21 may rely on the wrist band to disembark the cruise ship and to visit the museums and other attractions; the same wrist band may be used at other ports of call. The wrist band may have a useful life such that after return to home port, the wrist band is automatically disabled. When the wrist band incorporates an active RFID device, the battery powering the embedded active RFID device may be designed to have a lifespan shorter than normal for active RFID device batteries. Use of the herein disclosed wrist band, or other wearable device may expedite the process of disembarking and visiting, particularly when a cruise ship has thousands of passengers, while at the same time, meeting all safety requirements deemed necessary at the ports of call, at the attractions, and while onboard. Similar devices may be issued by tour companies, airlines, and other tourist entities. The same or similar devices may have applications beyond the tourist industry.

To begin an operation involving potential access by user 21 to one or more of the venues 7a-7n, the venue control 61 may display a list of access requirements for each of venues 7a-7n. The access requirements may include vaccinations, test sample results, and biometric data that may be used to confirm a user's identity and confirm the user's compliance with the access requirements of venues 7a-7n. User 21 may desire access to venue 7a, and in the course of attempting to acquire access, may be presented with the access requirements list. With the list available (displayed, for example, on smart device 20b), user 21 may be able to determine what, if any vaccinations or tests must be completed before accessing one of the venues 7a-7n.

Figure 4D:
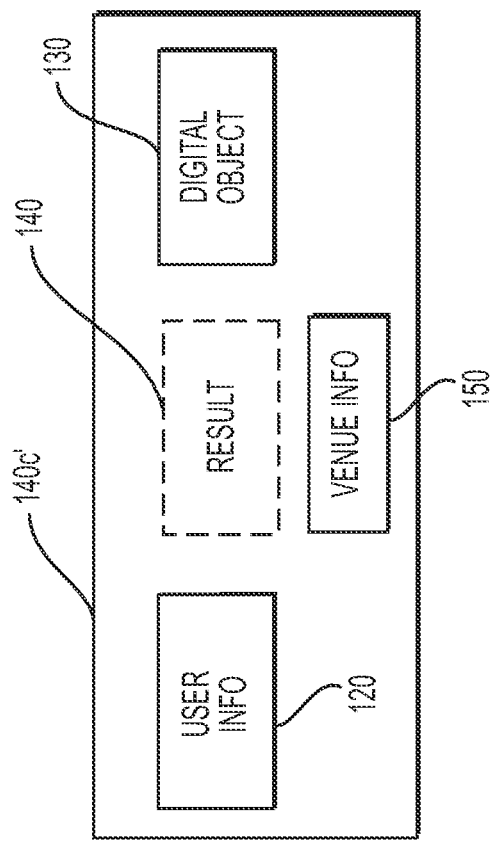
FIG. 4D illustrates an example printed certified access document.
Figure 4C:
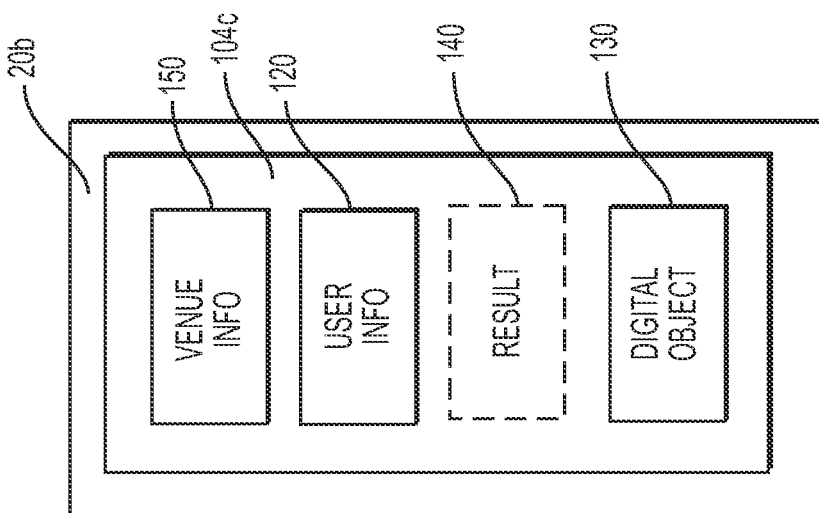
FIG. 4C illustrates an example digital certified access document.

FIG. 4C illustrates an example display of a digital certified access document 104c on smart device 20b. The document 104c includes user information 120; a digital object 130, which may be a two- or three-dimensional barcode, for example; optionally, a result 140, where appropriate and desired by user 21 or required by venue control 61; and venue information 150. The digital object 130 may encode vaccine information, test sample information, and user biometric information, for example. The digital object 130 may be a one-time scan digital object, a multiple-time scan digital object, or an unlimited-time scan digital object. Scanning the digital object 130 may result in access information (i.e., date, time, location of scan, and venue identify) being sent back to the venue control 61, and possibly back to the vaccine service 41, where the information may be used to update the user's account. Similar information may be recorded in the smart device 20b. In an aspect, an access control point may store the access information using a distributed ledger or blockchain architecture, and provide information in blocks that are added to a distributed ledger or blockchain maintained by the vaccine service 41. For example, each time a venue operator allows a user into a venue, the venue access point records the information about the health safety certification the venue control 61 received prior to allowing access to the user. In that way, the venue control 61 and/or the vaccine service 41 produces a chain of access record for every user allowed into the venue, with details about the health information that the venue control 61 relied on as being accurate; i.e., a ledger of use of the digital certified access document 104c.

FIG. 4D illustrates a printed certified access document 104c'. The printed document can be seen to include information similar to that of the digital version shown in FIG. 4C.

Figure 4E:
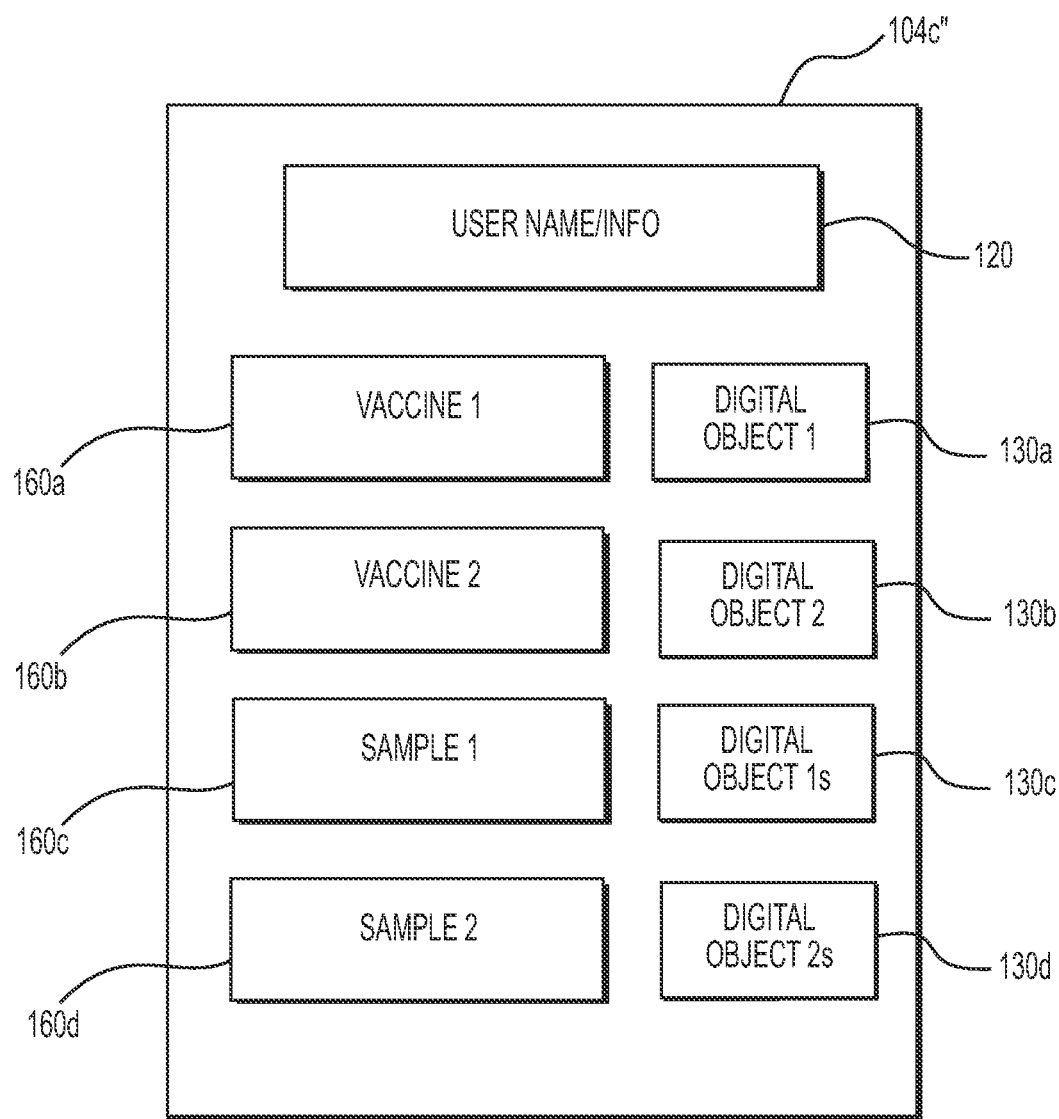
FIG. 4E illustrates another example digital certified access document.

FIG. 4E illustrates alternative digital certified access document 104c". The digital certified access document 104c" may be displayed on smart device 20b, or may be printed. The document 104c" includes user information 120. The document 104c" includes vaccine information 160a and 160b, and corresponding digital objects 130a and 130b. Similarly, the document 104c" may include test sample results 160c and 160d, and corresponding digital objects 130c and 130d. The document 104c" may be used to access any venue requiring vaccine 160a or 160b, or test samples 160c or 160d, providing the respective digital objects, when scanned, meet the access requirements of the venue. In an aspect, a venue may only access information contained in the digital certified access document 104c" that have been established (by, for example, venue control 61) as required for access to the venue. For example, if a venue requires only vaccination status for COVID-19, only that certification will be presented.

FIG. 4F illustrates smart device 20c with a health safety application 22c installed and providing display 118. In FIG. 4F, user 21 operates smart device 20c to provide various displays generated by application 22c. Also shown in FIG. 4F is venue access point 7a' (for venue 7a of FIG. 4B), which may include venue access point device 70. Venue access point device 70 may include a scanning component (not shown) and a display 71. Display 71 may provide a result window 72 and a user name window 73. The scanning component may be used to scan relevant components of the digital certified access document 104c, whether in digital form as shown in display 118 of FIG. 4F, or in printed form 104c' (see FIG. 4D). Display 118 includes scannable digital object 130e, which in an aspect, is a three-dimensional encoding. In a first aspect, the digital object 130e may include the results of any and all current sample test results and any and all current vaccinations. In one respect, "current" means the test results and vaccinations have not exceeded their assigned expiration dates, as established by the manufacturer, supplier, medical entity, or government agency, as appropriate, for the test sample or vaccination. In a second respect, "current" means the assigned time to live as set, in an example, by the venue control 61. In either respect, if a vaccination requires a waiting period (e.g., two weeks) before being considered effective, that vaccination information may not yet be encoded in the digital object 103e. In an aspect, the digital object 130e may include a cryptographically-encoded signature of user 21. In another aspect, digital object 130e may include biometric data of the user 21, which may be scanned to verify the identity of the user 21. For example, the biometric data may include a recent photograph of the user 21, and/or may include a thumbprint of the user 21. Other biometric data may be included in place of or in addition to the photograph and/or thumbprint. In still another aspect, the application 22c provides biometric information, and other identifying information, for user 21 in an area 132 of display 118 separate from the digital object 130e. For example, only the user's name may be displayed upon scanning the digital object 130e. In yet another aspect, after or before display of digital object 130e, the application 22c may present an interactive window 131 that may be used to capture, as an example, a thumbprint of user 21. In this further aspect, the digital object 130e may be rendered only after the application 22c is executed to determine a match between a stored thumbprint of user 21 and a thumbprint captured with the interactive window 131. In a still another aspect, the application 22c may transfer (e.g., by Bluetooth® 75) the biometric data of the user 21 (a thumbprint, retina scan, photograph, etc.) to a corresponding venue access point device 70 at the venue access point 7a'. The venue access point device 70 then may verify the identity of user 21. In one respect, the venue access point device 70 then may provide an identity-confirmed signal back to the smart device 20c, whereupon the application 22c causes display of the digital object 130e on the display 118. In another respect, the venue access point device 70 may confirm the identity, and the user 21 then may proceed with displaying the displaying the digital object 130e. In a still further aspect, communications between the application 22c executing on smart device 20c and the venue access point device 70 may incorporate the security aspects, features, mechanisms, systems, components, and methods of operation thereof illustrated in FIGS. 7A-7E, and disclosed in their accompanying descriptions. Including use of encoding, distributed ledgers, and blockchain functions. Furthermore, the digital object 130e may not be stored in the venue access point device 70, other than for the time of the comparisons described herein, and the digital object 130e may not be sent to the venue access point device 70, or scannable by the venue access point device 70 until the identity of user 21 has been confirmed. Still further, the venue access point device 70, and similarly the display 118, may only display a positive (e.g., pass) result (e.g., a check mark ("√") 72) or a negative (e.g., failure) results (e.g., an "X"). In still a further aspect, the venue access point device 70 may receive the digital certified access document 104c from either the smart device 20c (by way of venue control 61) or from the vaccine service 41 (also by way of venue control 61). Note that the digital certified access document 104c may include both test results and vaccination information. In this still further aspect, the application 22c and the venue access point device 70 may interact to confirm the identity of user 21 and to confirm that user 21 has met the test sample and vaccination requirements to access the venue 7a. In a yet another aspect, the application 22c operating on smart device 20c may be used over various networks to access services, products, and information. For example, user 21 may employ application 22c to schedule an Uber® trip, purchase an airline ticket or train ticket, schedule a face-to-face meeting with another user (e.g., a job interview, arrange a home decorator appointment, schedule a pedicure, schedule a doctor's appointment, meet with friends, etc.), and application 22c may execute to provide to a device operated by or for the benefit of the other user, the same or similar verifications as disclosed above for access to venue 7a. In one respect, the verifications may be conducted over a public-access network such as the Internet, and a confirmation may be provided to user 21 of acceptance of the appointment/meeting based on confirming operations executed at the other user's device.

FIG. 5 illustrates a generic kiosk 201 that may be implemented as a component of HSS system 200. The kiosk 201 may be installed at a point of sale of test kits (see, for example test kit 301 of FIG. 6) or supplies such as swabs that are used to collect a sample, such as at a pharmacy. The kiosk 201 may be installed at public access facilities such as museums for which separate access tickets are not required, at shopping malls, for example, and at indoor and outdoor facilities that generally are open to the public. The kiosk 201 may be installed at transportation hubs such as airports, train stations, or mass transit entry points. The kiosk 201 may be installed at a multi-tenant building or a hotel, resort, or casino.

The kiosk 201 includes camera 202, test platform 203, biometrics capture component 204, sample analyzer 205 and digital data input/output 206. The kiosk 201 may be connected to an AC power source, may be battery powered, or may be solar powered, or may be powered by a combination of the foregoing such that upon a loss of AC power, the kiosk 201 may continue to operate. The input/output 206 may include a visual display section or user interface and a mechanism such as a key pad or qwerty keyboard for data entry. The input/output 206 may connect to a wired or wireless data input to receive data from and send data to, for example, smart phone 20a and data merging service 50. To collect and analyze a sample, the kiosk 201 may provide in a user interface of the input/output 206, a menu of test options and instructions for completing a desired test. The kiosk 201 may be configured to acquire and analyze samples for a variety of illnesses. The desired test may be preceded by collection of image data of the user 21 through camera 202, where the image data may be digital still frame images, or video. If implemented, the test also may be preceded by collection of biometric information from the user 21, such as thumbprints. In a test operation, the kiosk 201 provides, through test platform 203, a sample collection device (e.g., a swab). After sample collection, the sample collection device is placed in a receptacle of the test platform 203 and the sample is read. The sample results may be transmitted to the analysis competent (analyzer) 205, where the reading is determined to indicate a negative or positive value, and/or, in some embodiments, to provide a quantitative value. The determined value is provided to the input/output 206, where the results may be displayed in the user-readable window or interface. The determined value is time-stamped, and data describing and identifying the kiosk, the sample obtained, the user 21, and the test performed are added to the time-stamped value to provide a certified test result that then may be transmitted to the user's smart phone 20a and/or the data merging service 50. In an event where the test result is not or cannot be certified, the test result may be provided to a certificate service (not shown in FIG. 5).

The herein disclosed embodiments of an HSS provide a significant technical advance over existing sample regimes and modalities at least in part because of incorporation of verifiable at-home testing afforded to users such as user 21 of FIG. 2, with the at-home testing capable of producing an authenticated and certified test result that may be employed to gain safe and secure access to a variety of venues over a defined period. For example, a single at-home test may allow access to air travel as well as theaters, sporting events, and other public events that may draw a large number of people.

Figure 6:
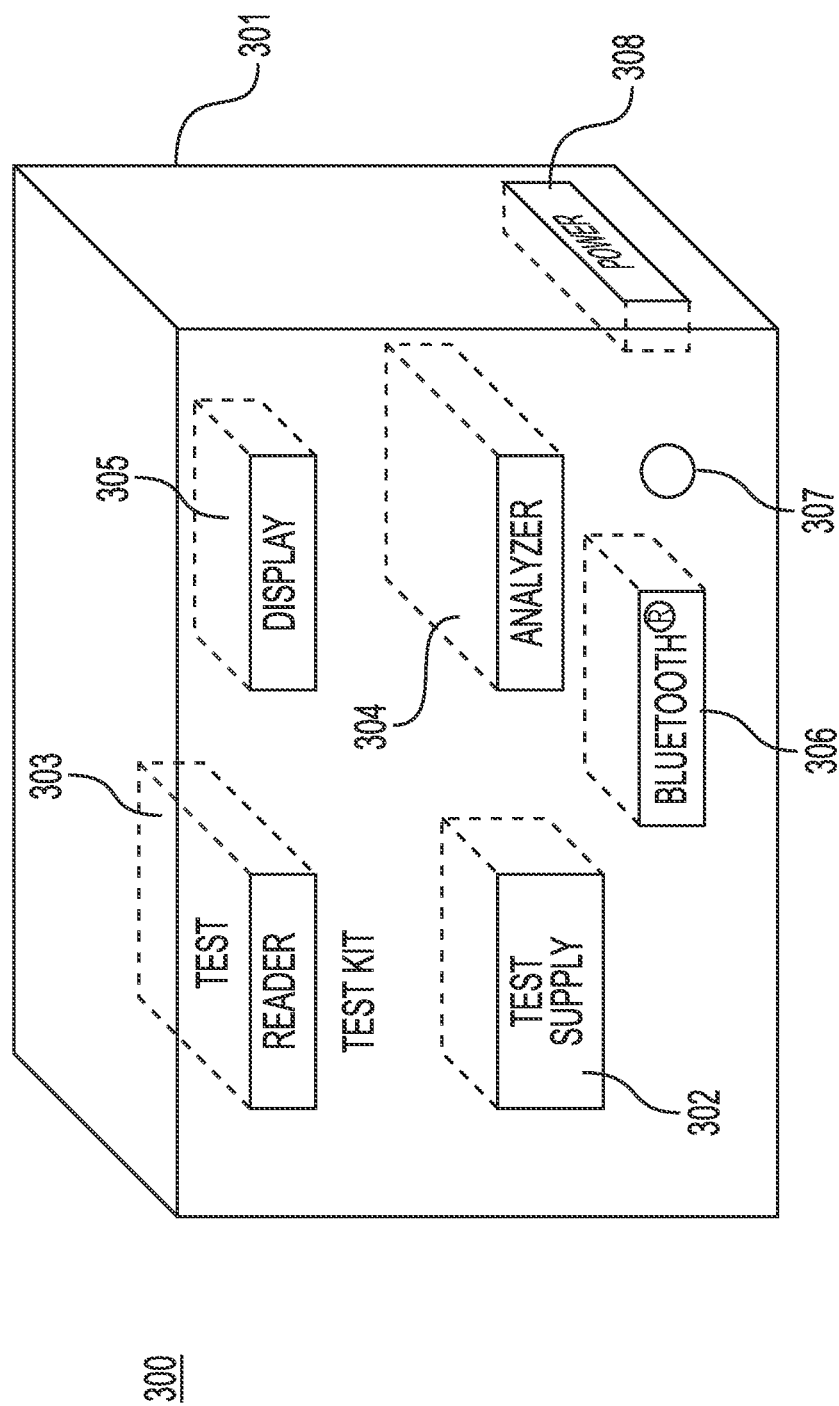
FIG. 6 illustrates an example test kit operable with the Health Safety Systems of FIGS. 1 and 2.

One aspect of an HSS is an at-home test kit, namely the rapid test platform 30 of FIG. 2. FIG. 6 illustrates an embodiment of an at-home test kit 301. The at-home test kit 301 may be a standalone device or may operate in cooperation with an application, such as application 22 of FIG. 2 installed on a smart device such as smart phone 20a of FIG. 2. In FIG. 6, at-home test kit 301, as part of HSS 300, is seen to include test sample acquisition supply 302, which may contain a swab or other sampling device. The kit 301 further includes a test reader 303 that reads the collected sample and analyzer 304 that determines a value of the read sample results. For example, the analyzer 304 may determine a read sample indicates the presence or absence of a virus, and may provide a quantitative value. A display 305 may present the sample result as determined by the analyzer 304 in a form and format that may be understood by a user. The display 305 also may display instructions for operation of the kit 301. The instructions may be provided by internal components of the kit 301 or by application 22 in communication with the test kit using wired connection 307 or wireless Bluetooth® connection 306. Finally, the kit 301 may include a battery power supply 308 with exchangeable batteries.

In an embodiment, the kit 301 is a one-time-use device. After a sample is received, analyzed and reported, the kit 301 may be incapable of any further function. In another embodiment, the kit 301 may be refurbished and reused, or may be employed by the same user 21 for one or more additional tests, including tests other than previously executed tests; that is, the kit 301 may be used for multiple, different modalities. In this embodiment, the kit 301 may employ a counter, and a current count may be included with a reported test. The number of tests that the kit 301 may execute may be limited, and the kit 301 may be unusable once the counter has reached a predetermined count.

In addition to the embodiments shown in FIGS. 1-6, as described herein, an HSS may be implemented in part at a medical clinic, facility, or hospital. For example, sample collection, analysis, and reporting may be performed at or initiated at a medical clinic. Further functions of the HSS may include those executed by the remaining components of FIG. 2, for example. Thus, a medical clinic may communicate test results to certification component 4 and data merge component 5. Such communications may be encrypted to ensure validity and authenticity of the reported test result, to prevent hacking, and to ensure compliance with all requirements in place to allow venue access.

Figure 7A:
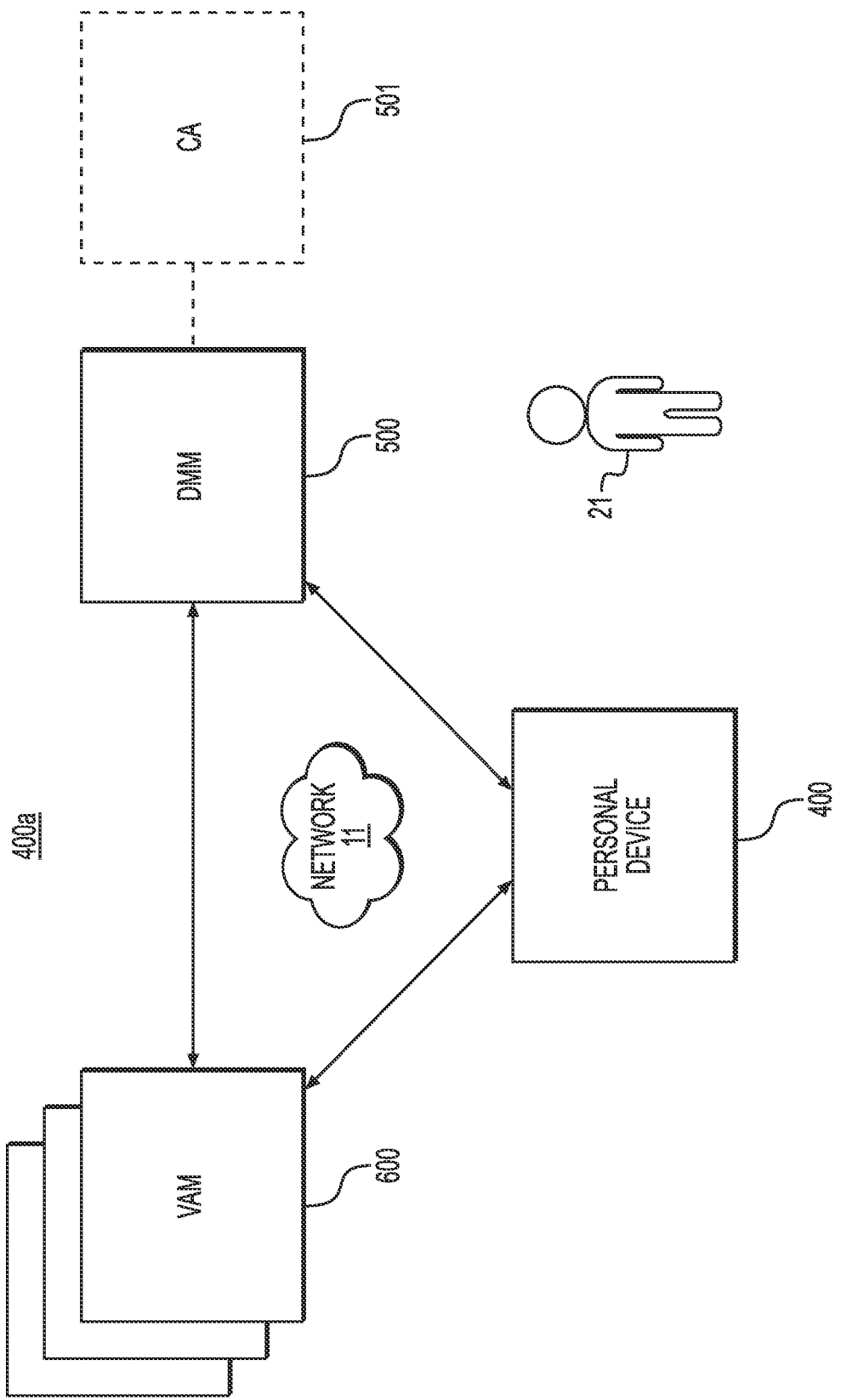
FIGS. 7A-7C illustrate another example Health Safety System, and components thereof.

FIG. 7A is a block diagram of entities in Health Safety System 400a. The entities include smart personal device (PD) 400 under control of user 21, data merging module (DMM) 500, and one or more venue access modules (VAM) 600. Optionally, the system 400a may include a separate certificate module 501. Otherwise, the certificate module 501 may be incorporated in the DMM 500. The entities shown in FIG. 7A may communicate over network 11.

Figure 7B:
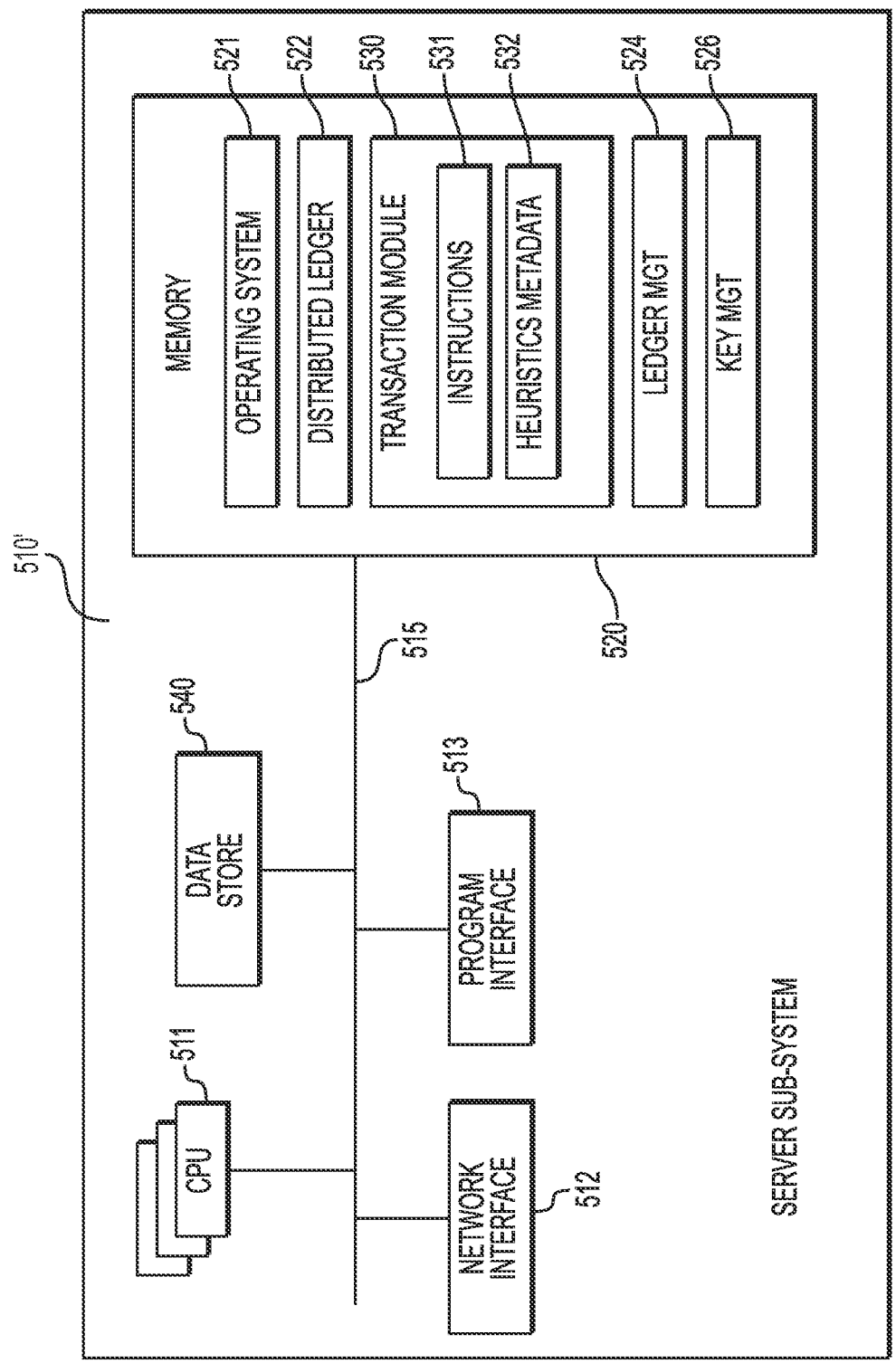

FIG. 7B shows illustrates portions of the DMM 500 in more detail. DMM 500 includes server sub-system 510'. Server sub-system 510' in turn includes one or more CPUs 511, network interface 512, program interface 513, and memory 520. Memory 520 is a non-transitory computer-readable memory. Memory 520 includes server operating system (OS) 521 and transaction module 530. Transaction module 530 includes machine instructions 531, which may be loaded from non-transitory computer-readable storage medium (i.e., data store) 540, and heuristics and metadata 532. The CPUs 511, network interface 512, program interface 513, memory 520, and data store 540 communicate over system bus 515. The operating system 521 includes procedures for handling various basic system services and for performing hardware dependent tasks. The transaction module 530 manages transactions between entities in the HSS 400a. For example, the transaction module 530 may transmit a key request to a network node within a cluster of network nodes (i.e., venue access components in VAM 600) that are configured to maintain a distributed ledger. The transaction module 530 receives a key in response to transmitting the key request, and synthesizes transaction data with the key. The transaction module 530 transmits the transaction data to another entity. In an aspect, the transaction module 530 is configured to perform the method 800 shown in FIG. 8. The transaction module 530 receives transaction data, transmits a validation request to determine whether the key utilized to synthesize the transaction data is valid, receives a validation response, and utilizes the transaction data to complete a transaction if the validation response indicates that the key is valid. The transaction module 530 is configured to perform the method 800 shown in FIG. 8. To that end, the transaction module 530 includes machine instructions 531, and heuristics and metadata 532.

The memory 520 and/or the data store 540 also stores programs, modules and data structures to enable a distributed ledger 522, a ledger management module 524, and a key management module 526. The distributed ledger 522 may be distributed over various network nodes. In an aspect, each network node stores a local copy of the distributed ledger 522. The distributed ledger 522 may store information regarding transactions between different entities in the HSS 400a. In an aspect, the distributed ledger 522 stores a batch of transactions in a block. In an aspect, each block is timestamped. The ledger management module 524 manages the distributed ledger 522. For example, the ledger management module 524 functions to ensure that the local copy of the distributed ledger 522 is synchronized with the local copy of the distributed ledger 522 at other network nodes. In an aspect, the ledger management module 524 participates in consensus protocols associated with the distributed ledger 522. For example, the ledger management module 524 may propose new blocks for the distributed ledger 522 and/or votes on block proposals received from other network nodes. To that end, the ledger management module 524 includes machine instructions, and heuristics, and metadata. The key management module 526 receives a key request from an entity, determines whether the key request is valid, synthesizes a key if the key request is valid, transmits the key to the entity, and stores the key in the distributed ledger 522. The key management module 526 determines whether the key request is valid by determining whether one or more validation criterion stored in the distributed ledger 522 is satisfied. For example, the key management module 526 may execute the method 900 shown in FIG. 9. The key management module 526 receives a validation request from an entity, accesses the distributed ledger 522 to determine whether the key utilized to synthesize the transaction data is valid, and transmits a validation response that indicates the validity status of the key to the entity. The key management module 526 performs the method 900 shown in FIG. 9. To that end, the key management module 526 includes machine instructions, heuristics, and metadata.

Figure 7C:
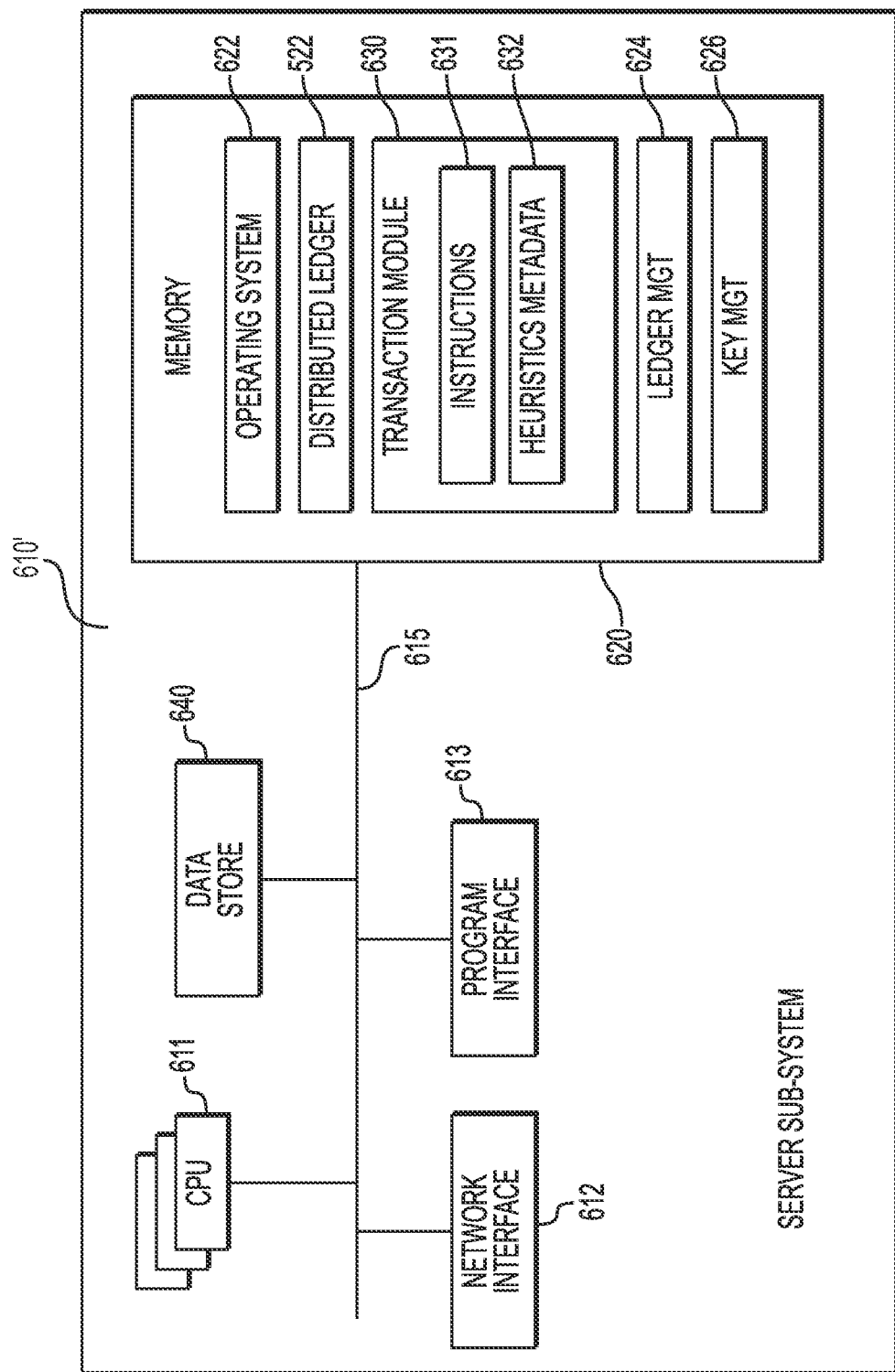

FIG. 7C illustrates the VAM 600 in more detail. In an embodiment, the VAM 600 may be enabled at various modules associated with and/or included in a network node of the network 11. The VAM 600 includes server sub-system 610', which in turn includes one or more processing units (CPUs) 611, network interface 612, program interface 613, a memory 620, data store 640, and communication bus 615. The memory 620 and/or the data store 640 stores programs, modules and data structures, or a subset thereof to include an operating system (OS) 622, a distributed ledger 522, a ledger management module 624, and a key management module 626. The distributed ledger 522, the ledger management module 624 and the key management module 626 may be similar to corresponding components of the DMM 500 shown in FIG. 7B. The operating system 622 includes procedures for handling various basic system services and for performing hardware dependent tasks. The distributed ledger 522 may be distributed over various network nodes. In an aspect, each network node stores a local copy of the distributed ledger 522. The distributed ledger 522 may store information regarding transactions between different entities in the HSS 400a. In an aspect, the distributed ledger 522 stores a batch of transactions in a block. In an aspect, each block is timestamped. The ledger management module 624 manages the distributed ledger 522. For example, the ledger management module 624 functions to ensure that the local copy of the distributed ledger 522 is synchronized with the local copy of the distributed ledger 522 at other network nodes. In an aspect, the ledger management module 624 participates in consensus protocols associated with the distributed ledger 522. For example, the ledger management module 624 may propose new blocks for the distributed ledger 522 and/or votes on block proposals received from other network nodes. To that end, the ledger management module 624 includes machine instructions and heuristics and metadata. The key management module 626 receives a key request from an entity, determines whether the key request is valid, synthesizes a key if the key request is valid, transmits the key to the entity, and stores the key in the distributed ledger 522. The key management module 626 determines whether the key request is valid by determining whether one or more validation criterion stored in the distributed ledger 522 is satisfied. For example, the key management module 626 performs the method 900 shown in FIG. 9. The key management module 626 receives a validation request from an entity, accesses the distributed ledger 522 to determine whether the key utilized to synthesize the transaction data is valid, and transmits a validation response that indicates the validity status of the key to the entity. To that end, the key management module 626 includes instructions and/or logic 631, and heuristics and meta data 632.

Figure 7D:
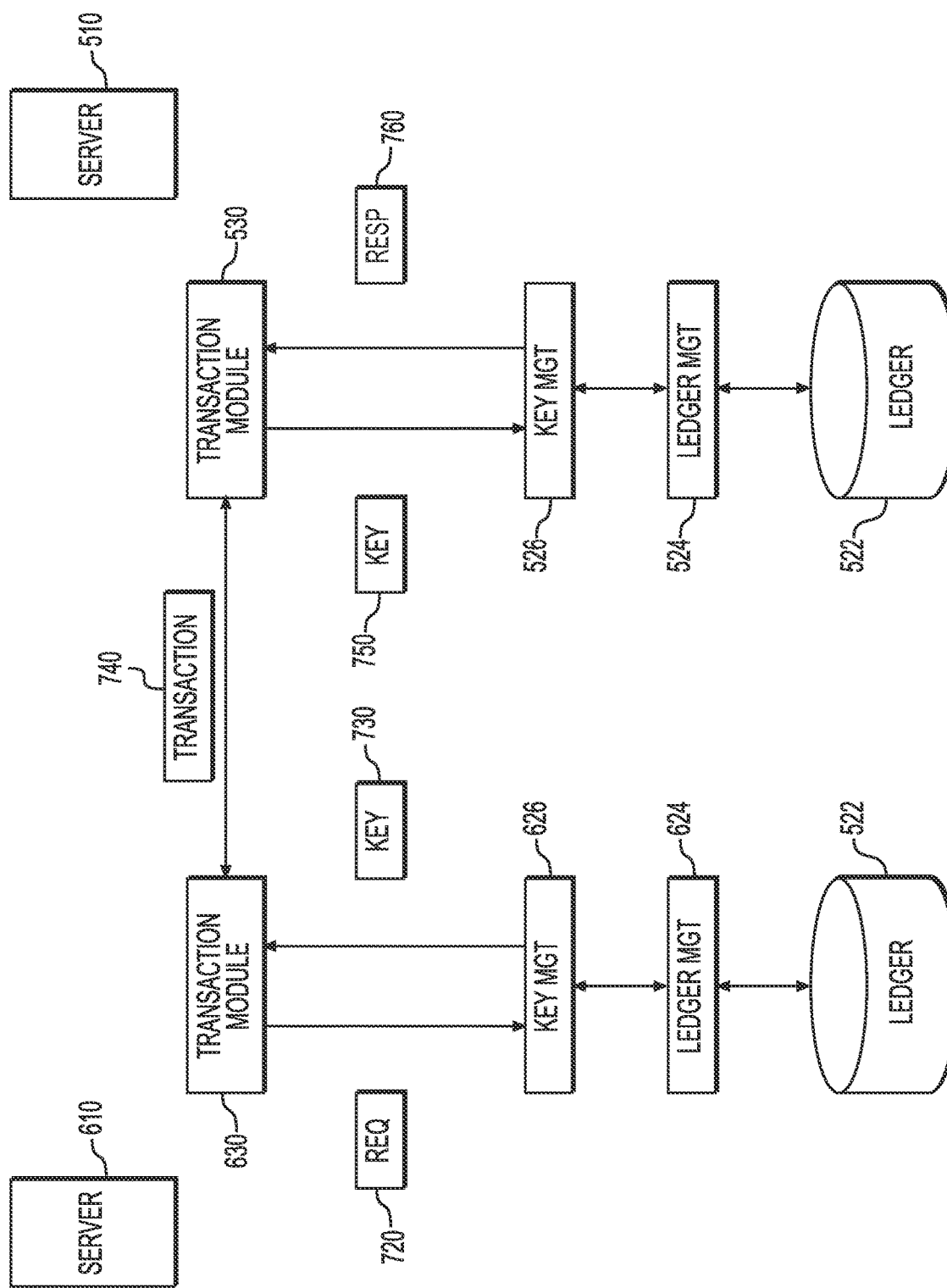
FIG. 7D illustrates an example transaction operation executable between components of the Health Safety System of FIGS. 7A-7C.

FIG. 7D illustrates a transaction operation between entities in the system 400a of FIG. 7A. In operation, the servers 510, 610 enable secure transaction between or on behalf of entities in the HSS 400a of FIG. 7A. For example, the servers 610 and 510 may execute transactions on behalf of a venue and user 21, respectively. To this end, each server 510 and 610 may implement a transaction module 530, 630. The transaction modules manage transactions between entities such as a venue and the smart personal device 400, and in an aspect, a transaction module may be associated with (e.g., owned by) one or more externally owned accounts that manage the transactions. In an example, a first externally owned account is controlled by user 21 while a second externally owned account is controlled by a venue or a venue's agent. As a result, the user 21 may have access to a private key that controls the externally owned account.

As FIG. 7A illustrates, the HSS 400a includes a cluster of network nodes (i.e., VAMs 600) connected by network 11. The VAMs 600 cooperate with the DMM 500 to generate and maintain a distributed ledger 522. In an aspect, each VAM 600 stores a local copy of the distributed ledger 522, and DMM 500 stores a complete copy of the ledger 522. Thus, in FIG. 7D, servers 510 and 610 store a copy of the distributed ledger 522. In an aspect, the distributed ledger 522 stores (e.g., records) transactions (e.g., all the transactions) between the entities (venues) represented by the VAMs 600 and the entity (smart personal device) 400. The distributed ledger 522 also may store metadata associated with the entities.

The distributed ledger 522 further may store contract accounts that include programs with computer-executable instructions. In an aspect, the contract accounts are associated with respective contract codes. In an aspect, the contract accounts correspond to respective externally owned accounts. In such aspects, the contract accounts are controlled by their corresponding externally owned accounts. As such, the distributed ledger 522 supports externally owned accounts and contract accounts. In an aspect, the distributed ledger 522 implements a data structure that includes various blocks, with each block holding a batch of individual transactions and including a timestamp indicating block inclusion in the ledger 522. The blocks also may, but need not, include information linking a succeeding block to a previous block. For example, a succeeding block includes a hash of a previous block. When implemented in this fashion, the distributed ledger 522 is referred to as a blockchain.

Each server 510, 610 may include a ledger management module, and a key management module, as shown in FIG. 7D. The ledger management modules manage the distributed ledger 522. For example, the ledger management modules may propose new blocks for the distributed ledger 522 (each proposed block containing one or more transactions). The ledger management module further performs operations to ensure that the network node includes an updated copy of the distributed ledger 522. For example, a ledger management module of a first VAM 600 performs operations to ensure that the local copy of the distributed ledger 522 stored at a first VAM 600 is the same as the local copy of the distributed ledger 522 stored at a second VAM 600. Generally, the ledger management module serves as an interface for the distributed ledger 522. For example, the key management module may access the distributed ledger 522 by way of the key management module.

In operation, a transaction module of server 610 may initiate a transaction with the server 510. For example, the smart personal device 400 may communicate with a venue represented by VAM 600 to access that venue. That is, an externally owned account associated with a venue determines to initiate a transaction with an externally owned account associated with the user 21. To execute this transaction, the transaction module of server 610 first may query the distributed ledger 522 to determine if a certification transaction is stored therein that would satisfy access requirements for the venue. The distributed ledger 522 may contain the certification transaction but not the required key. Alternately, the distributed ledger 522 may contain both the key and the certification transaction. Alternately, the distributed ledger 522 could contain neither. Assuming only the key is not available, the server 610 may request the server 510 provide the required key. In response, the transaction module transmits a key request 720 to the key management module 626. The key request 720 may indicate that the VAM 600 has determined to complete one or more transactions with the smart personal device 400. In an aspect, the key request 720 is to occur between the VAM 600 and the smart personal device 400. In an aspect, the key request 720 indicates a requested transaction type (e.g., health certification (i.e., the key request 720 is for a health credential that the transaction module requires to complete the transaction(s)).

In an aspect, the key management module 626 provides a key 730 in response to receiving the key request 720. In an aspect, the key management module 626 determines whether the key request 720 is a valid request. In an aspect, the key management module 626 accesses the distributed ledger 522 to determine whether the key request 720 satisfies one or more validation criterion. For example, the key management module 626 may query the distributed ledger 522 to determine whether the VAM 600 and the smart personal device 400 are permitted to transact with each other. In another example, the key management module 626 may query the distributed ledger 522 to determine whether the requested time duration, the requested number of transactions, and/or the requested transaction type are permitted. Other validation criteria also are possible. In yet another example, the key management module 626 may query the distributed ledger 522 to determine whether the smart personal device 400 has provided a preference for transactions.

In an aspect, the key management module 626 synthesizes the key 730. In an aspect, the key 730 may be a cryptographic key. In another aspect, the key 730 includes a session key, a pair of keys (e.g., a public key and a private key). In some examples, the pair of keys are asymmetric or a single shared key. For example, the key management module 626 may employ a variety of symmetric-key algorithms, such as Data Encryption Standard (DES) and Advanced Encryption Standard (AES), to generate the key 730. Alternately, the key management module employs a variety of public-key algorithms, such as RSA, to generate the key 730. In an aspect, the key 730 includes a random number. In another aspect, the key 730 is the output of a hash function, where the hash function is a hash of the names of the entities, a time of day, and/or a random number. In another aspect, the key 730 includes a credential. In a further aspect, the first key management module 626 may synthesize the key 730 by activating a contract account that is associated with an externally owned account associated with the first transaction module 630. For example, the first key management module 626 may execute instructions associated with the contract account. In this further aspect, the key request 720 may include a contract code for the contract account, and the first key management module 626 employs the contract code to activate the contract account.

In an aspect, the key 730 is associated with a key identifier (ID) that identifies the key, and a validity period that indicates a time duration during which the key 730 is valid. The validity period may be equal to a requested time duration. However, if the requested time duration is greater than a threshold time duration, the validity period may be limited to the threshold time duration. In a further aspect, the key 730 may be associated with a validity number that indicates a number of transactions that can be completed with the key 730. The validity number may be equal to a requested number of transactions. However, if the requested number of transactions is greater than a threshold number of transactions, the validity number may be limited to the threshold number of transactions. In a still further aspect, the key 730 is associated with a validity type that indicates a transaction type that may be completed with the key 720. The validity type may be the same as a requested transaction type. However, if the requested transaction type includes transaction types that are not permitted, the transaction may not be permitted. In an embodiment, the threshold time duration, the threshold number of transactions, and/or the permitted transaction types are represented by one or more validation criterion stored in the distributed ledger 522.

The transaction module 630 may employ the key 730 to synthesize the transaction data 740. In an aspect, the transaction data 740 includes signed data, and the transaction module 630 employs the key 730 to generate a digital signature and to sign the transaction data. In an aspect, the transaction module 630 signs the transaction data 740 (e.g., a hash of the transaction data) with the key 730. A person of ordinary skill in the art will appreciate that the transaction module 630 may employ a variety of signing techniques to synthesize the signed data. For example, the transaction module 630 may employ a Digital Signature Algorithm (DSA) and/or Elliptic Curve Digital Signature Algorithm (ECDSA) to synthesize the signed data. In an aspect, the transaction data 740 includes encrypted data. In this aspect, the transaction module 630 employs the key 730 to encrypt the transaction data 740. Other signing and/or encrypting techniques also are possible. When signed and encrypted, the transaction module 630 transmits the transaction data 740.

The transaction module 530 receives the transaction data 740 and completes the transaction based on the transaction data 740. The transaction module 530 may determine whether the transaction data 740 is valid by, for example, determining whether the key 730 employed to synthesize the transaction data 740 is valid. As such, the transaction module 530 transmits a validation request 750 to the key management module 526. In an aspect, the validation request 750 includes the key 730 (e.g., when the transaction data 740 includes the key 730). In another aspect, the validation request 750 includes the key ID. In yet another aspect, the validation request 750 includes only the transaction data 740. The key management module 526 receives the validation request 750 and determines whether the key 730 employed to synthesize the transaction data 740 is valid by, for example, querying the distributed ledger 522 with the key 730 and/or the key ID. The second key management module 526 then transmits a validation response 760 to the transaction module 530. The validation response 760 indicates a validity status of the key 730. For example, the validation response 760 may indicate the validity period, the validity number, and/or the validity type associated with the key 730 are satisfied.

Based on the validation response 760, transaction module 530 employs the transaction data 740 to complete the transaction. For example, the transaction module 530 may complete the transaction if the validation response 760 indicates that the transaction data 740 was synthesized with a valid key (e.g., the key 730 is valid). In an aspect, the transaction module 530 may further require a current time is within the validity period indicated by the validation response 760, that a current transaction type associated with the transaction data 740 is the same as the validity type indicated by the validation response 760, that a transaction counter indicates the number of transactions completed with the key 730 is less than the validity number indicated by the validation response 760. Note that some transactions when completed may involve executing a smart contract, or completing a money transfer. Thus, in a further aspect, the transaction module 530 may access the distributed ledger 522 to determine whether the transaction is permitted. If the distributed ledger 522 indicates that the transaction is permitted, the second transaction module 530 completes the transaction.

The architecture and method disclosed above are described as supporting testing and subsequent secure transmission of test results. Components of the same architecture may be used for other medical/health safety purposes. For example, the architecture of FIG. 1 may be used in conjunction with vaccine administration and subsequent reporting to various venues 7 to allow access to the venues 7 by user 21. Specifically, user 21 may desire, or be required, to obtain a vaccination in order to access a specific venue 7, where the venues include travel to, and return from, a foreign country (here, the venues 7 may be layered, such as airports, train stations, and ship terminals at the point of departure and entry of each country, as well as facilities at each country), take an ocean cruise, attend a university, enter a sports stadium of facility, or access other venues 7. Another example may involve taking a cruise to the Russian Federation. Normally, visitors to the Russian Federation are required to obtain a visa; however, passengers on a cruise liner are exempted for short (less than a day) shore visits, such as visiting Peterhof. However, the same passengers may be required to show proof of a specific vaccination or other health status in order to leave a passenger ship docked in a Russian Federation port. Furthermore, passengers who disembarked in a foreign country may be required to show proof of a vaccination or other health status to disembark without quarantine when returning to their home country. The herein disclosed health safety systems may be employed for the purposes noted immediately above, as well as for other use cases disclosed herein.

In situations involving vaccinations, operation of the health safety system may begin with user 21 visiting a medical facility (e.g., a hospital or clinic) or a pharmacy approved for administration of the vaccines. From a high level view, such a medical facility or pharmacy would, in addition to administering the vaccine, perform functions similar to those of the result transmission component 3 of FIG. 1 in that health care personnel at the medical facility or pharmacy would transmit a statement or certificate of administration to any or all of the certification component 4, data merge component 5, and venue access component 6, all or part of these three components constituting a health status provider. In operation, the user 21 may be registered with the health status provider, and the user 21 may give the medical facility or pharmacy with the user's health status provider account number. The medical health personnel, using the health status provider account number of the user 21 may upload information related to the vaccine administered to the user 21, the information including, for example, date of the vaccination; type of vaccination; time to effectiveness for the vaccine (i.e., the time required to build to immunity, which may be delayed for a period starting with the vaccination), and, if applicable, time of expected lapse of the vaccination; and, credentials of the medical facility/pharmacy and or health care provider. These data may be encrypted for delivery to the health status provider.

In an embodiment, the health status provider may generate a certificate of vaccination and may provide the certificate in response to venue queries. In an aspect, the certificate of vaccination may be a direct (e.g., a scanned image) replication of the data provided by a health care provider or medical facility. In another aspect, the certificate of vaccination may have appended thereto a machine-readable digital object or objects, including, but not limited to, a 2D barcode or a 3D barcode, or other appropriate digital object. In yet another aspect, the certificate of vaccination may be a digital record that includes the data provided by the health care provider or medical facility and further includes additional such as, for example, not only the aforementioned digital object, but also biometric data related to the user 21, such as fingerprints and an iris scan. The biometric data may be obtained separately from the vaccination (e.g., the biometric data may be obtained at a time prior to or subsequent to the vaccination. In still another aspect, the certificate of vaccination may be encapsulated in a distributed ledger, which further may use a blockchain architecture. Transactions (e.g., requesting certificates and receiving certificates in return) using a distributed ledger with or without a blockchain architecture are disclosed in the descriptions of FIGS. 7A to 7E with respect to test results. The same or a similar process would apply to transactions involving vaccinations.

For example, a cruise line, in order to allow user 21 to board a cruise ship (i.e., a venue) to St. Petersburg, Russian Federation, may require submission of a current vaccination. Furthermore, to disembark at St Petersburg in order to visit the Winter Palace, user 21 may have to provide proof of the vaccination. To provide the required vaccination certificate upon boarding and subsequently for disembarking, user 21 may visit a medical facility and receive the required vaccine, and the medical facility may upload the vaccination certificate to a health status provider or similar entity, where the vaccination certificate is verified, added to the user's account, and optionally encrypted. The health status provider then may receive a request for a vaccination certificate for user 21; the request may come from the user 21, from a specific venue agent (cruise line) or from a venue access service such as venue access component 6 of FIG. 1 or venue control 61 of FIG. 4B. In this example of a cruise, the vaccine certificate for user 21 may be supplied to the cruise line, which then ensures the vaccination certificate is provided to the cruise ship (the specific venue). Both the request for and transmission of the vaccination certificate may be end-to-end encrypted, as illustrated in FIG. 7D. Alternately or in addition, the vaccination certificate may be stored in a distributed ledger, and the venue access service may maintain a local copy of the distributed ledger. When the venue access service maintains a distributed ledger, the health service provider such as the vaccine service 41 of FIG. 4B may not receive the request; rather, the request is provided to the venue access service, such as the venue control 61. In an aspect, when a request is initiated by user 21, routing of the request may be handled by an application resident on the user's smart phone 20a such that the user 21 need not know how to address the request. In an aspect in which the venue access service (here, the cruise line) initiates the request, the user 21 may receive a notice that the venue access service requested the vaccination certificate. Continuing with the example of a cruise to St Petersburg, the cruise ship may supply the required vaccination certificate to port (customs) authorities in St Petersburg to allow user 21 to disembark. In an aspect, and to better ensure privacy for user 21, the vaccination certificate may take the form of a statement that user 21 is allowed to disembark, without specifying any medical information. This aspect may require some cooperation between the port authorities in St Petersburg and the cruise line. Furthermore, the cruise line may receive a vaccination certificate for user 21 and may generate a non-specific certificate (one that does not mention a specific vaccine) for use during disembarkation. In effect, the cruise line provides the certification as opposed to operating as a pass-through. As discussed herein, certificates, such as the vaccination certificate, may have a time to live. The time to live need not conform to the effective or expected life or effectiveness of the vaccine. When the time to live is reached, the vaccination certificate may be flushed from data storage in the health status provider, including in the distributed ledger. Similarly, if the vaccination certificate is assigned a maximum number of transactions (venue accesses), the certificate may be flushed from data storage. When a blockchain architecture is used with the distributed ledger, other mechanisms may be employed to ensure the vaccination certificate no longer may be used or accessed. For example, the blockchain architecture may implement mechanisms to edit transactions in blocks.

In an embodiment, rather than a health status provider transmitting the vaccination certificate to a venue, the health status provider may store (upload) the vaccination certificate in the user's account with the health status provider. In this embodiment, the vaccination certificate may be in the form of, but not limited to, a 2D or 3D bar code, or other machine-readable digital object, that contains the user's identity, or in an aspect, an anonymized user identity, and relevant information regarding the vaccine. The vaccination certificate also may include, as noted herein, biometric information of the user 21. The user 21 then may display the barcode on a screen of smart phone 20a, where the bar code may be read by an appropriate bar code reader at the point of entry to a venue. In this embodiment, user 21 may be provided the vaccination certificate by electronic mail, short message service, or other appropriate electronic means. Alternately, user 21 may access a portal at the health service provider and download the vaccination certificate. As with test results, the method and apparatus used to obtain and subsequently provide the vaccination certificate may be rated in terms of perceived security, such as highest, high, and medium, and specific venues 7 may specify a required security level.

In an embodiment, a transaction module may synthesize a digital wallet, which creates an externally owned account. For example, transaction module 530 of FIG. 7D may synthesize a digital wallet for user 21. The digital wallet may be implemented on smart personal device 400. The digital wallet allows user 21 to make online or other electronic purchases, and also provides user 21 with a convenient storage for certified access tickets, for example.

Figure 7E:
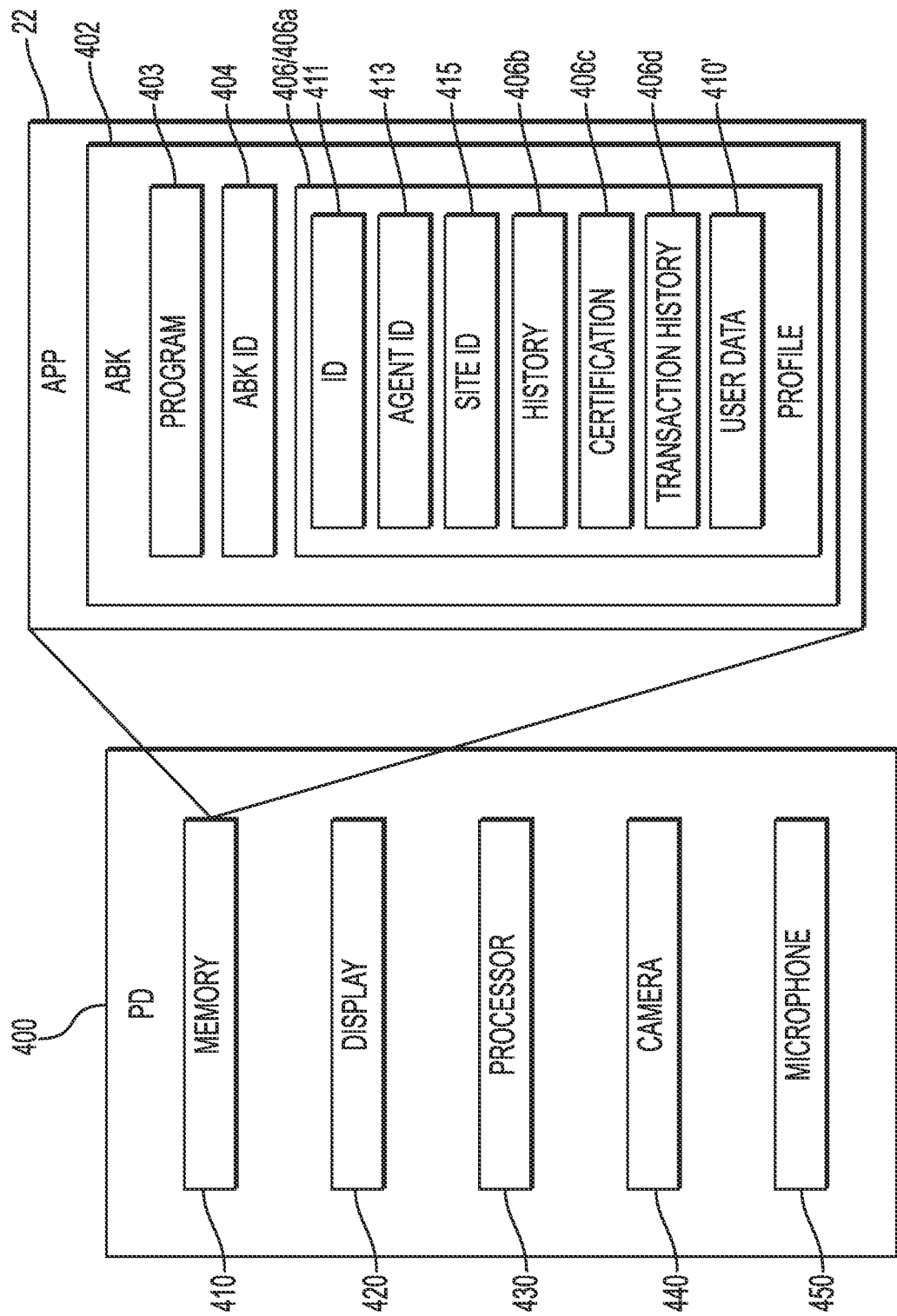
FIG. 7E illustrates an example Health Safety System application as implemented on a user's smart device.

FIG. 7E illustrates an example of an application biometric key (ABK) component 402. The ABK 402 resides in memory 410 of the smart personal device (PD) 400 and cooperates with software and hardware components of the PD 400, including display 420, processor 430, camera 440, and microphone 450. The ABK 402 may be implemented as part of application 22 of FIG. 1, and may be acquired and activated with acquisition and activation of application 22. However, application 22 may be operated without activation of ABK 402. Alternately, ABK 402 may be acquired and activated separately from application 22, but may cooperate with application 22. In another aspect, the functions of the ABK 402 may be implemented in a hardware device that may be integrated into the PD 400. The ABK 402 may be provided with a unique ABK ID 404 and one or more profiles 406. The ABK ID 404 may include a public section and a private section, each of which may be used for identification and authentication. In an embodiment, the ABK ID 404 may be stored in a read-only format. The ABK ID 404 may be employed as an identifying feature of the ABK 402 and distinguishes between ABKs 402 in the DMM 500 or VAM 600. The ABK 402 may include a program of instructions 403 by which the functions of the ABK 402 are executed.

The profile 406 may include user profile biometric data 406a, a profile history 406b, a profile certification 406c, a transaction history 406d, and other data 410'. Profile biometric data 406a, for example, includes data representing physical and/or behavioral information that can uniquely identify the user 21. The ABK 402 may operate to cause storage of multiple biometric profiles for user 21, each biometric profile for a different type of biometric data. In an embodiment, a biometric profile may include either or both digital data and analog data. The biometric profile may include a jpeg image. Profile biometric data 406a may be transformed by a mathematical operation, algorithm, or hash that represents the complete biometric information (e.g., a complete fingerprint scan, a complete retina scan). In an aspect, a mathematical hash may be a "one-way" operation such that there is no practical way to re-compute or recover the complete biometric information from the biometric profile. This both reduces the amount of data to be stored and protects the user's personal biometric information. In an aspect, the biometric profile is further protected by encoding using an encoding key and/or algorithm that is stored with the profile biometric data 406a. Then, for authentication, both the profile biometric data 406a and the encoding key and/or algorithm are passed to the DMM 500/VAM 600.

In an embodiment, the ABK 402 operates to cause storage of a picture profile that includes one or more jpeg or analog images of the user 21. In a picture authentication operation, the image stored in the ABK 402 may be transmitted to a display at the point of entry of a venue to allow an administrator (e.g., a clerk or security guard) to confirm or reject the identity of the user 21 requesting venue access. In another embodiment, an image of the user 21 may be captured at the point of entry and is compared to the picture profile by an image analysis mechanism of the application 22 or an independent autonomous and automated device associated with the point of entry. In a point of entry at, for example a hotel, casino, or restaurant, a host could greet the user 21 and allow entry based on recognition of the user's picture profile. The DMM 500 may receive the encoded profile biometric data 406a from the smart personal device 400 and may use the biometric data 406a as part of a certification process.

In an embodiment, the ABK 402 may automatically transmit encoded biometric data 406a to the DMM 500 when, for example, the user 21 selects this option in the application 22, and when the user 21 applies for access to a venue. In an embodiment, some profile biometric data 406a may be acquired by operation of the ABK 402 during a trusted initialization process that is administered by a trusted agent. In an embodiment, once initial profile biometric data 406a have been stored by operation of the ABK 402, the user 21 may add information through operation of the ABK 402 without a trusted agent through self-authentication. For example, an ABK 402 that has an associated stored biometric profile may be unlocked by providing a matching biometric input. Once unlocked, the user 21 may add or remove additional biometric profiles, credit card data, personal information, and other information through operation of the ABK 402. For example, in one embodiment, a user who has unlocked the ABK 402 may store additional biometric information (such as fingerprint information in addition to an existing retina scan).

The profile history 406b includes an ID field 411, an agent ID field 413, and a site ID field 415. The profile history 406b relates to the specific hardware, trusted agent, and site used at the time the profile biometric data 406a were created and stored by operation of the ABK 402. In an aspect, each profile 406 stores its specific profile history 406a along with the profile biometric data 406a and other profile data. The profile history 406b may be recalled for auditing purposes at a later time to ensure the credibility of the stored data. In an embodiment, transaction history 406d also may be stored to a user data segment of the PD memory 410. Here, the ABK 402 stores information associated with any transactions made with the ABK 402, such as the venue name, date of access, and purchase amount. In an aspect, the transaction history may be stored using distributed ledger and blockchain techniques.

The ABK 402 also may include programming to implement a biometric reader through cooperation with hardware and software components of the PD 400. For example, fingerprints, retina scans, and image may be captured through employment of an interactive display screen/interface 420 and camera 440, of the PD 400, as appropriate.

Figure 8:
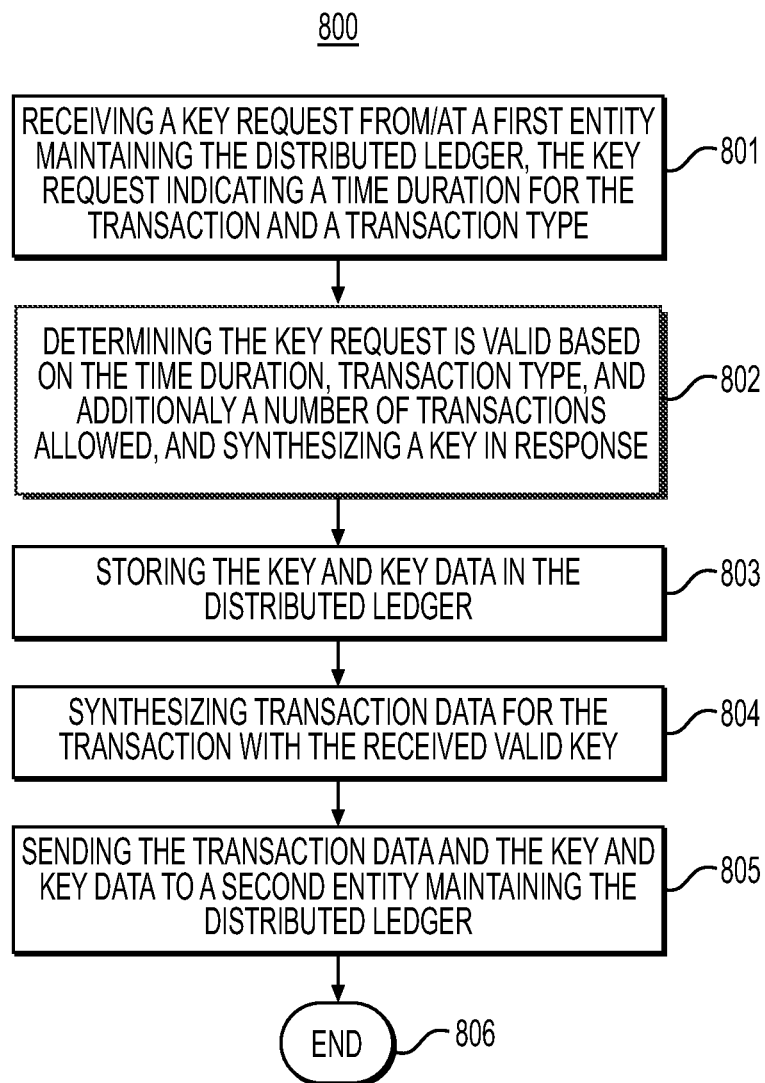
FIGS. 8 and 9 are flowcharts illustrating example operations of the Health Safety System of FIGS. 7A-7C, and components thereof.

FIG. 8 is a flowchart illustrating an example operation 800 of components shown in FIGS. 7A-7E. For example, operation 800, as illustrated, may be performed by either the DMM 500 or the VAM 600. Operation 800 begins in block 801 when a first entity, such as the VAM 600, receives a key request. The key request may be associated with an operation to be executed at the first entity, such as approving or certifying a transaction that involves access to a venue associated with the VAM 600. For example, the user 21, operating PD 400, may attempt to purchase a concert ticket for a venue associated with the VAM 600. For this transaction (purchase a ticket) to be approved, the user may be required to supply, or have supplied on behalf of the user 21, the user's health status. Note that if the concert is well after the purchase date (as might be normal), the HSS 10 may operate to require the user 21 to supply, or have supplied, a health certificate within a defined time window, such as 24 hours, before the concert date/time. However, for ease of illustration, the operation 800 will be further described assuming the certification and ticket purchase are contemporaneous. In this situation, the distributed ledger 522 may contain a block storing the user certification and other data necessary to grant access to the concert venue. (Note that any VAM 600 or the DMM 500 may propose a block for addition to the distributed ledger 522.) Thus, the first entity proceeds with block 802 to determine if the key request is valid. Validity may be based on one or more criteria including is the key request valid based on a predetermined time duration value, a number of times the key has been used compared to an allowed use number (note that a key may, in some embodiments, be used only once), the transaction type (e.g., purchase a ticket), and other validity criteria. When the key request is determined to be valid, the first entity synthesizes a key as part of the operation of block 802. In block 803, the first entity stores the key and any associated key data (e.g., key ID) in the distributed ledger 522, making the key accessible to any entity having access to the distributed ledger 522. Using the synthesized key, the first entity synthesizes (signs) the transaction, block 804. In block 805, the first entity sends the transaction, key, and key ID to the second entity. Operation 800 then ends, block 806.

Figure 9:
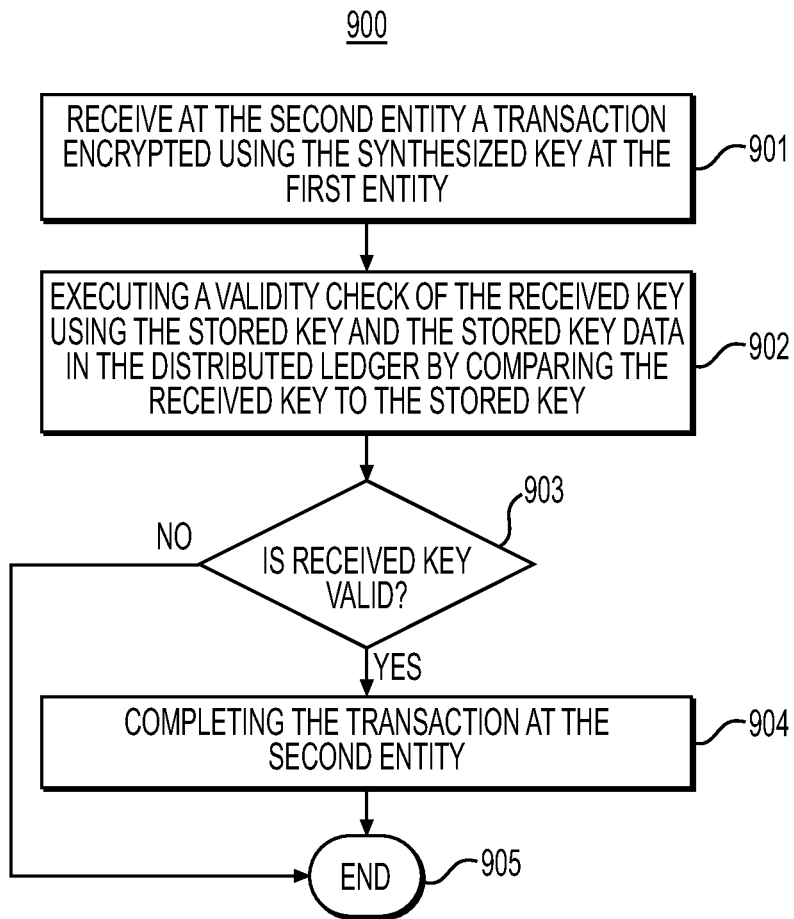

FIG. 9 is a flowchart illustrating another example operation of the components shown in FIGS. 7A-7E. For example, operation 900, as illustrated may be performed by either the DMM 500 or the VAM 600. Operation 900 begins in block 901 after receipt of the signed transaction sent in block 805 of FIG. 8. In block 902, the second entity executes a validity check of the key received with the transaction in block 901 by retrieving the key from the ledger 522 and comparing the retrieve key and the received key. In block 903, the second entity determines whether or not the received key is valid. If in block 903, the key is determined to be valid, operation 900 moves to block 904 and the second entity completes the transaction. If the key is not valid, or following block 904, operation 900 moves to block 905 and ends.

Figure 10:
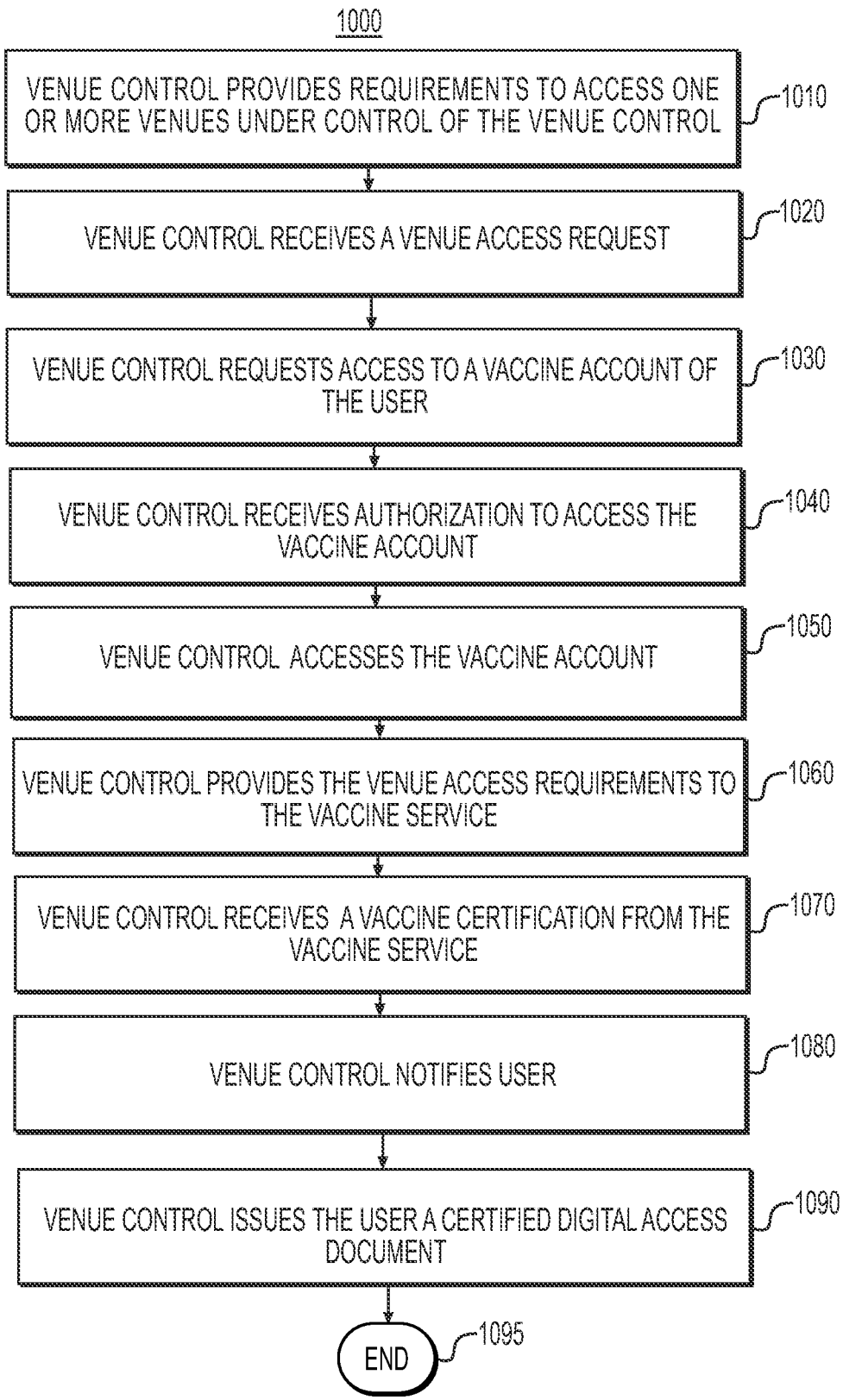
FIG. 10 is a flowchart illustrating other example operation of the Health Safety System of FIGS. 7A-7C.

FIG. 10 is a flow chart illustrating example vaccine process 1000 in which a venue control, such as the venue access component 6 of FIG. 1 or the venue control 61 of FIG. 4B, cooperates with a health, or vaccine, service to facilitate user access to venues, such as venues 7a-7n, that require proof of vaccination. Process 1000 beings in block 1010 when a processor at a venue control 61 provides requirements to allow users, such as user 21, to access one or more venues 7a-7n under control of the venue control 61; one such requirement may be the user 21 providing a certification of a current vaccine in order to access a venue. In block 1020, the processor receives a venue access request from user 21, requesting access to a venue 7a-7n controlled by the venue control 61. In an aspect, the venue control 61 may control access to multiple venues types or to a single venue type. As an example, the venue control 61 may control access to various sports stadiums in a metropolitan area; may control access to airports in a foreign country. Alternately, the venue control 61 may be an airline with domestic and international flights, and the airline, operating as a venue control, functions to process and verify compliance with whatever proof of vaccination the destination may require. For example, a flight from Boston to Paris may require a vaccination certificate to enter France, and the airline operates to process and verify the vaccination certificate. Likewise, a cruise line may operate as a venue control for all ports of call to be made by a cruise ship. In another alternative, a separate entity or service may perform the vaccine verifications and provide the required certifications to allow access by the user 21 at the venue access point. In still another aspect, the venue control 61 may issue a digital certified access document 104*c*/104*c*″ that is recognized and accepted at multiple, unrelated venues. For example, the venue control 61 may provide a digital certified access document 104/104*c*″ that is accepted at ports of entry in specific foreign countries regardless of the carrier. T certified document may be an electronic or digital certified document, or may be a printed certified access document 104*c*′. The certification of the document may be embedded in a digital object that is scanned at a point of departure and/or at a point of arrival (i.e., a venue access point). The certified access documents 104*c*, 104*c*′ may be for a one-time use, or limited (prescribed) number of uses, or may be useable for the time period for which the vaccine is considered valid. In block 1030, the venue control 61 requests access to a vaccine account of the user; the vaccine account of the user 21. may be maintained by the vaccine service 41, or another service. The vaccine account of the user 21 may include certified data, such as certificates 4*a* and 4*b* of FIG. 1, or the digital certified access documents 104*c*, 104*c*″ for one or more vaccines administered to the user 21, the certified data being obtained from medical facilities such as medical facility 105 administering the vaccines. Alternately, the vaccine account of the user 21 may be maintained on the user's smart device such as smart device 20*b*. In block 1040, the venue control 61 receives authorization from the user 21 to access the vaccine account of the user 21. In an aspect, the authorization may be implicitly or explicitly given with submission of a venue access request. In block 1050, the venue control 61 accesses the vaccine account of user 21. In block 1060, the venue control 61 provides the venue access requirements to the vaccine service 41. In block 1070, the venue control 61 receives a certification (a digital certificate) from the vaccine service 41 that provides proof that the venue access requirements are met for the user 21. In optional block 1080, the venue control 61 notifies user 21 (e.g., by SMS or email) that the venue access requirements are met. In block 1090, the venue control 61 issues the user a digital certified access document 104*c* to access the venue. In block 1095, method 1000 ends. In an aspect, the transactions disclosed above may incorporate the security featured disclosed with respect to FIG. 7D, including use of distributed ledger and blockchain architectures.

In the method 1000 of FIG. 10, the certified digital access document 104*c* may comprise a one-time read digital object. Alternately, the certified digital access document 104*c* comprises a digital object with a time to live, and may be used for multiple venue accesses. In an aspect, the certified digital access document 104*c* is provided by an application of the service installed on a smart device 20*b* designated by the user 21, and the certified digital access document 104*c* is displayable on the smart device 20*b* and scannable at an access point of the venue. In another aspect, the certified medical facility 105 provides the certified data of the current vaccine to the vaccine service 41 for inclusion in the user's vaccine account and also may send the certified data to the user's registered smart device 20*b*.

In another aspect, the method 1000 may include a requirement comprising verification of one or more biometric samples uniquely identifying the user, the biometric samples comprising one or more of a fingerprint, a retina scan, an image for facial recognition, and a voice recording for speech recognition, wherein the biometric samples are stored in the vaccine account of the user. In a further aspect, the biometric samples are provided to the user for storage on the smart device of the user. In still a further aspect, the service provides the vaccine data for the user for display on the smart device designated by the user.

In another aspect, to display the vaccine data for the user 21 on the smart device 20*b*, the user 21 submits a contemporaneous biometric sample matching at least one of the biometric samples stored in either the vaccine account of the user and the smart device 20*b* of the user. The fingerprints biometric sample of the user 21 may be provided to the venue for verification of the contemporaneous biometric sample of the user 21. The biometric sample may be obtained from the vaccine service 41, a kiosk, or an application resident on the user's smart device 20*b*. The biometric sample may be a voice recording, a facial image, a retina scan, a fingerprint.

In another aspect, the certified digital access document 104*c* requires submitting at least one biometric sample at the venue access point as part of a process for venue access.

Alternately, the certified digital access document 104*c* is printed for accessing the venue and then is scanned at the venue access point.

In an aspect, the certified digital access document 104*c* guarantees all venue access requirements are met without displaying any vaccine data or user personal information.

In an aspect, user 21 may request, and the vaccine service 41 may provide, one or more certified copies of a previously-issued certified digital access document 104*c*, provided the previously-issued certified digital access document 104*c* has not been scanned at an access point of the venue.

In an aspect, the certified digital access document 104*c* grants access to additional venues operated by the venue control 61 and having access requirements identical to those required by a successfully-accessed venue.

Figure 11:
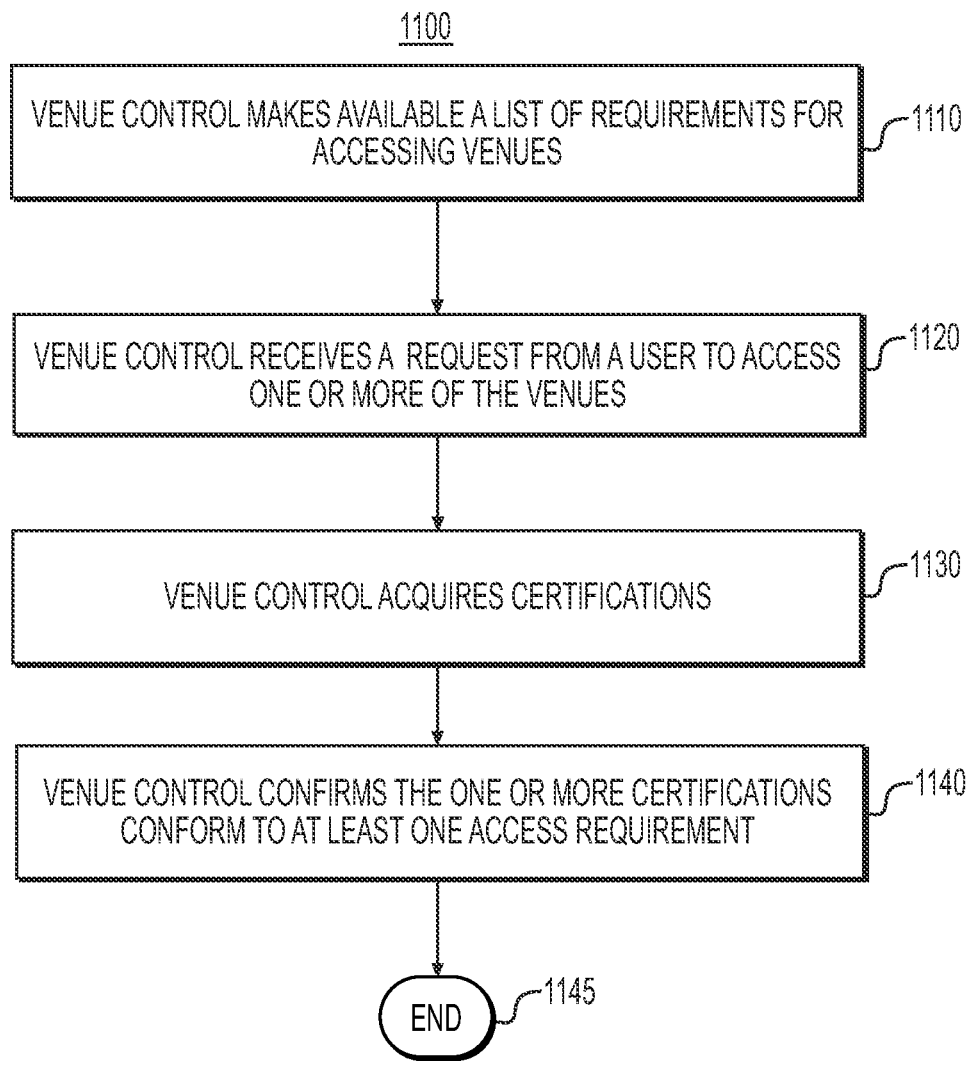
FIG. 11 is a flowchart illustrating yet another example operation of the Health Safety System of FIGS. 7A-7C.

FIG. 11 is a flowchart illustrating yet another health safety method. In FIG. 11, health safety method 1100 begins in block 1110 when a processor associated with venue access control, such as venue control 61 of FIG. 4B, provides, or otherwise makes available to user 21, a list of requirements for accessing venues 7*a*-7*n*. For example, the list may include a certified vaccination, a certified anti-body/antigen test result, and a certified test for absence of a virus or other infectious disease. The list also may include a requirement to submit a verifiable representation of a biometric sample. Alternately, a separate service may provide the list. In block 1120, the processor receives a request from user 21 to access one or more of the venues 7*a*-7*n*. In an aspect, the request may include an explicit permission from user 21, to the venue control 61 to acquire the one or more certifications from a health account of the user 21. Alternately, the permission to acquire the certifications may take place using a separate permission process. In yet another alternative, the user 21 may direct the entity holding the user's certifications to supply the requisite certifications to the venue control 61.

In still another alternative, the user 21 may supply the requisite certifications from the user's smart phone 20*a*. In block 1130, the processor acquires the one or more certifications. In block 1140, the processor confirms the one or more certifications conform to at least one requirement in the list. In block 1150, the venue control 61 issues to the user 21, a certified digital document 104*b*/104*c* granting access to the requested venues. In block 1045, the method 1100 ends.

In some situations, a local health safety provider may implement the above-disclosed methods, or aspects thereof, in a local health safety system. For example, a university, a large multi-building industrial plant, a cruise line, or an amusement park may instantiate aspects of a local health safety system. In an aspect, the local health safety provider operates only at the local level (i.e., venues "on-site" or otherwise directly associated with the university, industrial plant, cruise line, and amusement park), and does not provide health safety of user 21 to any "third-party" venues. In an aspect, the local health safety system is used for initial entry of user 21 to a venue such as an industrial plant. That is, user 21 may present a test certificate for a first entry to the industrial plant. Subsequent entry for a defined period also may be covered by the test certificate. After the defined period, further entry may require a renewed test certificate. Alternately or in addition, the test certificate, as noted herein, may have a defined time to live. In a university setting, a prospective student may be required to present a current vaccination safety to gain admission. The university may incorporate this requirement into operation of a local health safety system, and may use the local health safety system for subsequent testing, vaccinations, and inoculations.

In operation, user 21 may be tested or vaccinated on site, at home, or at and third location and that test result may send to the local-level health safety system. Any restricted areas on-site may require the user 21 to provide an ID in the form of a badge, ticket or wristband, thumb print, etc. that would identify the user 21 uniquely. Based on the presented ID of the user 21, the health safety system would query its stored health safety records before allowing admission to the restricted area. Note that in some settings (industrial plant, amusement park), the entire facility may be restricted. In these settings, the user's health safety might only be accessed at an initial point of entry of plant or park. After an initial health safety check the user 21 may be granted unlimited access to all plant or park locations for a limited time. In this scenario, the local network maintains some safety information after a single initial query to the health safety provider.

In a university setting, access to university buildings may be restricted. In this setting, a campus health safety system may operate to provide a certificate to the user 21 for smart phone 20*a*, and the user 21 may present the certificate at specific locations on the campus as well as at third party venues. This aspect eliminates the need for the campus health safety system to directly communicate with third-party venues. Thus, if the user 21 goes off campus for lunch the user 21 may be able to access a restaurant by displaying a test certificate on the smart phone 20*a*.

Following are additional example operating scenarios, and corresponding method steps, in which an HSS as disclosed herein (see, e.g., FIGS. 1-6) may be employed to enhance security and safety at a venue while ensuring the privacy of attendee data.

User 21 plans to take an airplane trip and the airline requires Sars-Cov-2 testing within 24 hours of boarding the flight. In step A, user 21 creates an account at the HSS 10 and receives an account ID. In step B, within 24 hours of boarding, the user 21 acquires a home Sars-Cov-2 test kit (e.g., kit 301 of FIG. 6). The test kit 301 comes with a unique test ID and is connected to the user's smart phone 20*a*. In step C, the user 21 performs the home test and receives a test result on smart phone 20*a*. In step D, using application 22 on smart phone 20*a*, the user 21 forwards the test result along with an attestation that these results are from a test that the user 21 self-performed, to the certificate service 40. In step E, the user 21 signs into an airline website to acquire a boarding pass. In step F, the user 21 receives a message from the airline system prompting the user 21 to provide a Sars-Cov2-test result before a boarding pass is issued. In step G, the user 21 enters the HSS account ID. In an aspect, the user 21 could provide the password to the HSS account to the airline, enabling the airline to provide valid credentials to the HSS 10 (the DMS 50) for retrieval of the test certification; alternately, the user could wait to be contacted from the HSS 10 to authorize release of the user's health certificate to the airline. Following completion of step G, the HSS 10 provides a test certification to the airline that the user 21 has had a negative test result within 24 hours prior to the boarding time.

User 21 wants to order an UBER driver and the driver requires a negative Flu A/B test within the prior 24 hours. In step A1, if user 21 already has an HSP account, the user 21 simply takes the home test and submit the results to the HSS 10. In step B1, an Uber application on smart phone 20*a* asks the user 21 to provide a health safety certification prior to ordering an UBER driver. In step C1, user 21 enters the HSSP account ID. In step D1, Uber contacts the HSS 10 for health safety verification. In step E1, the HSS notifies user 21 that Uber has requested their health safety and the user authorizes the release of the user's health safety to UBER. In step F1, UBER receives the health safety and schedules the driver.

User 21 works at a meat-packing plant and must periodically update the HSS account with valid test results, as required by the company. In step A2, Company has the user's HSS account ID in the company's personnel records and checks at regular intervals that the employee is actively getting tested. Alternately, Company provides a regular testing facility on site and mandates that its personnel get tested there. In step B2, user 21 employs the HSS account ID for access to other venues by proving the user 21 are disease free and to maintain the proof.

In addition to application to testing as a medical procedure, the additional operating scenarios and the local health systems disclosed above, may apply to medical procedures such as vaccination and inoculation. For example, the same or a similar process for obtaining an airplane boarding pass based on a test result may apply to obtaining an airplane boarding pass based on a vaccination.

Thus, the preceding specification discloses methods, techniques, systems, and components to be used in testing for infectious diseases and in vaccinating for infectious diseases. The specification similarly discloses methods, techniques, systems, and components for inoculations. As one skilled in the art will understand, the methods, techniques, systems, and components disclosed may be applied, as appropriate to the specific medical procedure, to any testing, vaccination, or inoculation. One skilled in the art will further understand that aspects of the methods, techniques, systems, and components may be applied to other medical procedures such as, for example, an EKG, and other medical procedures.

The preceding disclosure refers to flowcharts and accompanying descriptions to illustrate the embodiments represented in FIGS. 7D, 8, and 9. The disclosed devices, components, and systems contemplate using or implementing any suitable technique for performing the steps illustrated. Thus, FIGS. 7D, 8, and 9 are for illustration purposes only and the described or similar steps may be performed at any appropriate time, including concurrently, individually, or in combination. In addition, many of the steps in the flow chart may take place simultaneously and/or in different orders than as shown and described. Moreover, the disclosed systems may use processes and methods with additional, fewer, and/or different steps.

Embodiments disclosed herein can be implemented in digital electronic circuitry, or in computer software, firmware, or hardware, including the herein disclosed structures and their equivalents. Some embodiments can be implemented as one or more computer programs; i.e., one or more modules of computer program instructions, encoded on computer storage medium for execution by one or more processors. A computer storage medium can be, or can be included in, a computer-readable storage device, a computer-readable storage substrate, or a random or serial access memory. The computer storage medium can also be, or can be included in, one or more separate physical components or media such as multiple CDs, disks, or other storage devices. The computer readable storage medium does not include a transitory signal.

The herein disclosed methods can be implemented as operations performed by a processor on data stored on one or more computer-readable storage devices or received from other sources.

A computer program (also known as a program, module, engine, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

We claim:

1. A health safety method, comprising:
a health safety kiosk established at a venue access point of venue control, the venue control providing requirements to allow users to access one or more venues under control of the venue control, the requirements comprising a certification of a current vaccine, wherein the health safety kiosk comprises:
a display and user interface component,
a communications component, and
a processor in communication with and controlling operation of the display and user interface component and the communications component, wherein the method comprises:

the processor receiving an access request, from a user through the display and user interface component, requesting access to a venue controlled by the venue control;
the processor through the display and user interface component, requesting access to a vaccine account of the user, the vaccine account of the user maintained by a vaccine service, the vaccine account of the user comprising certified data for one or more vaccines administered to the user, the certified data obtained from medical facilities administering the vaccines;
the processor receiving authorization from the user to access the vaccine account of the user;
the processor accessing the vaccine account of the user;
the processor providing the venue access requirements to the vaccine service;
the processor receiving certification from the vaccine service that the venue access requirements are met for the user;
the processor notifying the user that the venue access requirements are met; and
the processor issuing the user a certified digital access document to access the venue.

2. The health safety method of claim 1, wherein the certified digital access document comprises a one-time read digital object.

3. The health safety method of claim 1, wherein the certified digital access document comprises a digital object with a time to live.

4. The health safety method of claim 1, wherein the certified digital access document is provided by an application of the service installed on a smart device designated by the user, wherein the certified digital access document is displayable on the smart device and scannable at an access point of the venue.

5. The health safety method of claim 4, wherein a certified medical facility provides the certified data of the current vaccine for inclusion in the user's vaccine account.

6. The health safety method of claim 1, the requirements further comprising verification of one or more biometric samples uniquely identifying the user, the biometric samples comprising one or more of fingerprints, a retina scan, an image for facial recognition, and a voice recording for speech recognition, wherein the biometric samples are stored in the vaccine account of the user.

7. The health safety method of claim 6, wherein the biometric samples are provided to the user for storage on a smart device of the user.

8. The health safety method of claim 7, wherein the service provides the vaccine data for the user for display on the smart device designated by the user.

9. The health safety method of claim 8, wherein to display the vaccine data for the user on the smart device, the user submits a contemporaneous biometric sample matching at least one of the biometric samples stored in one of the vaccine account of the user and the smart device of the user.

10. The health safety method of claim 9, wherein the biometric sample of the user is provided to the venue for verification of the contemporaneous biometric sample of the user.

11. The health safety method of claim 6, wherein the certified digital access document requires submitting at least one biometric sample at a venue access point as part of a process for venue access.

12. The health safety method of claim 1, wherein the certified digital access document is printed for accessing the venue.

13. The health safety method of claim 1, wherein the certified digital access document guarantees all venue access requirements are met without displaying any vaccine data.

14. The health safety method of claim 1, wherein the user requests, and the service provides, one or more certified copies of a previously-issued certified digital access document, provided the previously-issued certified digital access document has not been scanned at an access point of the venue.

15. The health safety method of claim 1, wherein the certified digital access document grants access to additional venues operated by the venue control and having access requirements identical to those of the venue.

16. A health safety system implemented by a venue control, the health safety system, comprising:
a health safety kiosk established at a venue access point, the health safety kiosk, comprising
a processor,
a display and user interface component,
a communications component, and
a non-transitory, computer readable storage medium having encoded thereon, machine instructions, wherein the processor executes the machine instructions to:
provide requirements to allow users to access one or more venues under control of the venue control, the requirements comprising a certification of a current vaccine;
receive through the display and user interface component, an access request, from a user, requesting access to a first venue controlled by the venue control;
request through the display and user interface component, access to a vaccine account of the user, the vaccine account of the user maintained by a vaccine service, the vaccine account of the user comprising certified data for one or more vaccines administered to the user, the certified data obtained from medical facilities administering the vaccines;
receive through the display and user interface component, an authorization from the user to access the vaccine account of the user;
access through the communications component, the vaccine account of the user;
provide through the communications component, the venue access requirements to the vaccine service;
receive through the communications component, certification from the vaccine service that the venue access requirements are met for the user for the first venue;
notify through the display and user interface component, the user that the first venue access requirements are met; and
issue through the display and user interface component, the user a certified digital access document to access the first venue, wherein the certified digital access document is configured for storage on a smart device of the user.

17. The health safety system of claim 16, wherein the vaccine service provides the vaccine data for storage, display, and scanning on a smart device designated by the user.

18. The health safety system of claim 17,
wherein the requirements further comprise verification of one or more biometric samples uniquely identifying the user, the one or more biometric samples selected from a biometric group consisting of fingerprints, a retina scan, an image for facial recognition, and a voice recording for speech recognition;
wherein the biometric samples are stored in the vaccine account of the user; and
wherein to display the vaccine data for the user on the smart device, the user submits a contemporaneous biometric sample, at the display and user interface control, matching at least one of the biometric samples stored in at least one of the vaccine account of the user and the smart device of the user.

19. The health safety system of claim 16, wherein the certified digital access document comprises a digital object with a configurable time to live.

20. A health safety method implemented on a health safety kiosk established at a venue access point for a first venue, the health safety kiosk comprising a processor, the method, comprising:
providing by the processor, a list of requirements for accessing the first venue, the list consisting of one or more certifications selected from a first group consisting of a certified vaccination, a certified anti-body/antigen test result, and a certified test for absence of a virus;
receiving by the processor, a request from a user to access the first venue, the request comprising a permission allowing the processor to acquire the one or more certifications from a health account of the user;
using the permission, the processor acquiring the one or more certifications from the health account;
confirming the one or more certifications conform to at least one requirement in the first group; and
issuing to the user a certified digital document granting access to the first venue.

21. The health safety method of claim 20, wherein the health account is maintained on a smart device operated by the user.

22. The health safety method of claim 20, wherein the health account is maintained by a third-party service.

23. The health safety method of claim 20, wherein the digital document is a certified digital ticket comprising a scannable digital object comprising data consisting of the one or more certifications.

24. The health safety method of claim 23,
wherein the requirements further comprise verification of one or more digital biometric data objects uniquely identifying the user, the digital biometric data objects selected from a second group consisting of one or more fingerprints, a retina scan, a facial recognition map, and a digital voice recording, and
wherein the method further comprises:
acquiring at least one digital biometric data object from the health account;
comparing the acquired at least one digital biometric data object to a contemporaneous biometric object obtained from the user; and
confirming the contemporaneous biometric object matches the acquired at least one digital biometric data object prior to issuing the digital document.

25. The health safety method of claim 24, wherein the certified digital ticket provides access to multiple venues requiring at least one certification from the first group.

26. The health safety method of claim 24, wherein the certified digital ticket provides access only to the first venue.

27. A health safety system, comprising:
a health safety kiosk established at a venue access point, the health safety kiosk, comprising;
a processor,
display and user interface component,
a communications component, and
a non-transitory, computer-readable storage medium having encoded thereon machine instructions for implementing a health safety system and method, wherein the processor executes the machine instructions to:

provide a list of requirements for accessing a first venue, the list consisting of one or more certifications selected from a first group consisting of a certified vaccination, a certified anti-body/antigen test result, and a certified test for absence of a virus;

receive a request from a user to access the first venue, the request comprising a permission to acquire the one or more certifications from a health account of the user;

use the permission to acquire the one or more certifications from the health account;

confirm the one or more certifications conform to at least one requirement in the first group; and issue to the user a certified digital document granting access to the first venue.

28. The system of claim 27, wherein the digital document is a certified digital ticket comprising a scannable digital object comprising data consisting of the one or more certifications.

29. The system of claim 27, wherein the requirements further comprise verification of one or more digital biometric data objects uniquely identifying the user, the digital biometric data objects selected from a second group consisting of one or more fingerprints, a retina scan, a facial recognition map, and a digital voice recording, wherein the processor:

acquires at least one digital biometric data object from the health account;

compares the acquired at least one digital biometric data object to a contemporaneous biometric object obtained from the user; and confirms the contemporaneous biometric object matches the acquired at least one digital biometric data object prior to issuing the digital document.

30. The system of claim 27, wherein the certified digital document provides access to multiple venues requiring at least one certification from the first group.

* * * * *